(12) United States Patent
Ali et al.

(10) Patent No.: US 7,994,198 B2
(45) Date of Patent: Aug. 9, 2011

(54) PIPERIDINETRIOL DERIVATIVES AS INHIBITORS OF GLYCOSYLCERAMIDSYNTHASE

(75) Inventors: Mezher Hussein Ali, Slough (GB); Michael Glen Orchard, Slough (GB)

(73) Assignee: Actelion Pharmaceuticals Ltd., Allschwil (CH)

( * ) Notice: Subject to any disclaimer, the term of this patent is extended or adjusted under 35 U.S.C. 154(b) by 1076 days.

(21) Appl. No.: 10/522,207

(22) PCT Filed: Jul. 17, 2003

(86) PCT No.: PCT/GB03/03244
§ 371 (c)(1), (2), (4) Date: Oct. 27, 2005

(87) PCT Pub. No.: WO2004/007454
PCT Pub. Date: Jan. 22, 2004

(65) Prior Publication Data
US 2006/0111400 A1 May 25, 2006

(30) Foreign Application Priority Data

Jul. 17, 2002 (GB) .................................. 0216656.9
Jan. 22, 2003 (GB) .................................. 0301480.0
Jun. 13, 2003 (GB) .................................. 0313674.4

(51) Int. Cl.
*A61K 31/445* (2006.01)
*C07D 211/36* (2006.01)

(52) U.S. Cl. ......................... 514/327; 546/219

(58) Field of Classification Search .................. 514/328; 546/219
See application file for complete search history.

(56) References Cited

U.S. PATENT DOCUMENTS

| | | | |
|---|---|---|---|
| 4,407,809 A | 10/1983 | Junge et al. | |
| 4,639,436 A * | 1/1987 | Junge et al. | 514/24 |
| 4,639,463 A | 1/1987 | Rosner et al. | |
| 5,003,072 A * | 3/1991 | Partis et al. | 546/243 |
| 5,051,407 A * | 9/1991 | Boshagen et al. | 514/24 |
| 5,276,120 A * | 1/1994 | Wong et al. | 546/184 |
| 5,798,366 A | 8/1998 | Platt et al. | |
| 6,046,214 A | 4/2000 | Kristiansen et al. | |
| 6,225,325 B1 * | 5/2001 | Jacob | 514/328 |
| 6,426,198 B1 | 7/2002 | Carstea et al. | |
| 6,495,570 B2 | 12/2002 | Jacob et al. | |
| 6,683,076 B2 | 1/2004 | Walkley et al. | |
| 7,256,005 B2 * | 8/2007 | Zitzmann et al. | 435/7.2 |
| 2001/0044453 A1 | 11/2001 | Jacob et al. | |
| 2004/0019082 A1 | 1/2004 | van der Spoel et al. | |
| 2006/0058349 A1 | 3/2006 | Hussein et al. | |
| 2006/0074107 A1 | 4/2006 | Butters et al. | |
| 2006/0111400 A1 | 5/2006 | Hussein et al. | |
| 2007/0112028 A1 | 5/2007 | Orchard et al. | |
| 2007/0259918 A1 | 11/2007 | Orchard | |
| 2008/0234324 A1 | 9/2008 | Scopes et al. | |

FOREIGN PATENT DOCUMENTS

| | | |
|---|---|---|
| DE | 3024901 A | 1/1982 |
| EP | 0491041 | 6/1992 |
| EP | 0 536 402 A1 | 4/1993 |
| EP | 0536402 | 4/1993 |
| EP | 0 698 012 B1 | 1/1997 |
| JP | H02-306962 | 12/1990 |
| WO | WO 92/00277 | 1/1992 |
| WO | WO 94/26714 | 11/1994 |
| WO | WO 98/02161 | 1/1998 |
| WO | WO 98/30219 | 7/1998 |
| WO | WO 99/24401 | 5/1999 |
| WO | WO 00/33843 | 6/2000 |
| WO | WO 00/56334 | 9/2000 |
| WO | WO 00/62780 | 10/2000 |
| WO | WO 01/10429 | 2/2001 |
| WO | WO 02/055498 A1 | 7/2002 |
| WO | WO 2004/007453 | 1/2004 |
| WO | WO 2004/007454 | 1/2004 |
| WO | WO 2004/111001 | 12/2004 |
| WO | WO 2004/111002 | 12/2004 |
| WO | WO 2005/068426 | 7/2005 |

OTHER PUBLICATIONS

Boeshagen et al. "use of 2-hydroxymethyl . . . " CA 113:126581(1990).*
Ezure et al. "Preparation of 1-deoxy . . . " CA 116:236093 (1992).*
Broek et al. "Chemical modification . . . " CA 119:96007 (1993).*
Berg et al. "Herbicidal composition . . . " CA 96:117597(1982).*
Kurihara et al. "Preparation of N-substi . . . " CA 114:185939 (1991).*
Kato et al. "Biological properties of . . ." J. Med. Chem. 48 p. 2036-44 (2005).*
Prodrug definition MedicineNet.com (from internet) p. 1 (2009).*
Abe, A., et al., "Reduction of globotriaosylceramide in fabry disease mice by substrate deprivation," *J. Clin. Invest.*, 2000, 105(11), 1563-1571.
Alessandri, G., et al., "Angiogenic and angiostatic microenvironment in tumors,"*Acta. Oncol.*, 1997, 36, 383-387.
Alter, M., "GM1 ganglioside for acute ischemic stroke—trial design issues," *Ann. NY Acad. Sci.*, 1998, 845, 391-401.
Bramer, S.L., et al., "Biologic activity of 5'-deoxy-5-fluorouridine by rectal administration,"*Pharmaceutical Res.*, 1989, 6(4), 318-322.
Chatterjee, S., et al., "Role of lactosylceramide and MAP kinase in the proliferation of proximal tubular cells in human polycystic kidney disease,"*J. of Lipid. Res.*, 1996, 37, 1334-1344.

(Continued)

*Primary Examiner* — Celia Chang
(74) *Attorney, Agent, or Firm* — Hoxie & Associates LLC

(57) ABSTRACT

Compounds of formula (I); wherein R represents various substituent groups, are useful as inhibitors of glucosylceramide synthase.

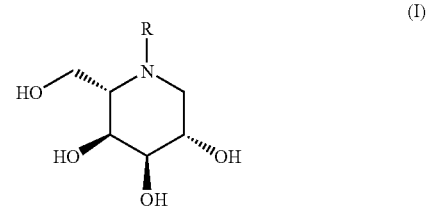

(I)

13 Claims, No Drawings

OTHER PUBLICATIONS

Chen, C.-S., et al., "Abnormal transport along the lysosomal pathway in mucolipidosis, type IV disease," *Proc. Natl. Acad. Sci. USA*, 1998, 95, 6373-6378.

Choo-Smith, L.-P., et al., "Acceleration of amyloid fibril formation by specific binding of Aβ-(1-40) peptide to ganglioside-containing membrane vesicles," *J. of Biol. Chem.*, 1997, 272(37), 22987-22990.

Cox, T., et al., "Novel oral treatment of Gaucher's disease with N-butyldeoxynojirimycin (OBT 918) to decrease substrate biosynthesis," *The Lancet*, 2000, 355, 1481-1485.

De Man, P., et al., "Bacterial adherence as a virulence factor in urinary tract infection,"*APMIS*, 1990, 98, 1053-1060.

Fowler, P.A., et al., "Synthesis and activity towards yeast α-glucosidase of 1,5-dideoxy-1,5-imino-L-iditol (1-deoxy-L-idonojirimycin)," *Carbohydr. Res.*, 1993, 246, 377-381.

Geisler, F.H., "Clinical trials of pharmacotherapy for spinal cord injury," *Ann. NY Acad. Sci.*, 1998, 845, 374-381.

Goodman, L.A., et al., "Ectopic dendrites occur only on cortical pyramidal cells containing elevated GM2 ganglioside in α-mannosidosis," *Proc. Natl. Acad. Sci. USA*, 1991, 88, 11330-11334.

Handa, K., et al., "Analysis of glycolipid-dependent cell adhesion based on carbohydrate-carbohydrate interaction," *Methods in Enzymol.*, 2000, 312, 447-458.

Hansson, G.C., et al., "A novel approach to the study of glycolipid receptors for viruses,"*FEBS Lett.*, 1984, 170(1),15-18.

Jaranowska, A., et al., "Platelet-activating factor production by human fetal microglia,"*Mol. & Chem. Neuropathol.*, 1995, 24, 95-106.

Jimenez-Lucho, V., et al., "*Cryptococcus neoformans, Candida albicans,* and other fungi bind specifically to the glycosphingolipid lactosylceramide (Galβ1-4Glcβ1-1Cer), a possible adhesion receptor for yeasts,"*Infect. & Immun.*, 1990, 58(7), 2085-2090.

Jeyakumar, M., et al., "Delayed symptom onset and increased life expectancy in Sandhoff disease mice treated with N-butyldeoxynojirimycin," *Proc. Natl. Acad. Sci. USA*, 1999, 96, 6388-6393.

Lavie, Y., et al., "Agents that reverse multidrug resistance, tamoxifen, verapamil, and cyclosporine A, block glycosphingolipid metabolism by inhibiting ceramide glycosylation in human cancer cells,"*J. of Biol. Chem.*, 1997, 272(3), 1682-1687.

Li, R., et al., "Cellular gangliosides promote growth factor-induced proliferation of fibroblasts,"*J. of Biol. Chem.*, 2000, 275(44), 34213-34223.

Lingwood, C.A., et al., "Analysis of interactions between glycosphingolipids and microbial toxins,"*Methods in Enzymol.*, 2000, 312, 459-473.

Liu, Y.-Y., et al., "Uncoupling ceramide glycosylation by transfection of glucosylceramide synthase antisense reverses adriamycin resistance," *J. Biol. Chem.*, 2000, 275(10), 7138-7143.

Lucci, A., et al., "Glucosylceramide: a marker for multiple-drug resistant cancers,"*Anticancer Res.*, 1998, 18, 475-480.

McKallip, R., et al., "Tumor gangliosides inhibit the tumor-specific immune response," *J. Immunol.*, 1999, 163, 3718-3726.

Memon, R.A., et al., "Regulation of glycosphingolipid metabolism in liver during the acute phase response," *J. Of Biol. Chem.*, 1999, 274(28), 19707-19713.

Memon, R.A., et al., "Regulation of sphingolipid and glycosphingolipid metabolism in extrahepatic tissues by endotoxin," *J. of Lipid. Res.*, 2001, 42, 452-459.

Merrer, Y.L., et al., "Synthesis of azasugars as potent inhibitors of glycosidases," 1997, 5(3), 519-533.

Nicholson, K.M., et al., "Preferential killing of multidrug-resistant KB cells by inhibitors of glucosylceramide synthase," *Br. J. Cancer*, 1999, 81(3), 423-430.

Overkleeft, H.S., et al., "Generation of specific deoxynojirimycin-type inhibitors of the non-lysosomal glucosylceramidase," *J. of Biol. Chem.*, 1998, 273(41), 26522-26527.

Platt, F.M., et al., "N-butyldeoxygalactonojirimycin inhibits glycolipid biosynthesis but does not affect N-linked oligosaccharide processing," *J. Biol. Chem.*, 1994, 269(43), 27108-27114.

Platt, F.M., et al, "Prevention of lysosomal storage in tay-sachs mice treated with N-butyldeoxynojirimycin," *Science*, 1997, 276, 428-431.

Poitout, L., et al., "Synthesis of azasugars. Part 1—Simerization of polyhydroxylated piperidines," *Tetrahedron Letts.*, 1996, 3 7(10), 1609-1612.

Prokazova, N. V., et al., "Gangliosides and atherosclerosis,"*Lipids*, 1994, 29, 1-5.

Rao, V.S., et al., "Regioselective eliminations in reactions of carbohydrate derivatives with superoxide, or with borohydride in 2-propanol," *Can. J. Chem.*, 1981, 59(2), 333-338.

Ryan, J.L., et al., "Changes in membrane gangliosides: differentiation of human and murine monocytic cells," *Yale J. of Biol. Med.*, 1985, 58, 125-131.

Schneider, J.S., "GM1 ganglioside in the treatment of Parkinson's Disease," *Ann. NY. Acad. Sci.*, 1998, 845, 363-373.

Simons, K., et al., "Functional rafts in cell membranes," *Nature*, 1997, 387, 569-572.

Svensson, M., et al., "Carbohydrate receptor depletion as an antimicrobial strategy for prevention of urinary tract infection," *J. of Infect. Dis.*, 2001, 183(*Suppl. 1*), S70-S73.

Yanagisawa, K., et al., "GM1 ganglioside-bound amyloid β-protein (Aβ): a possible form of preamyloid in Alzheimer's disease," *Nat. Med.*, 1995, 1(10), 1062-1066.

Yohe, H.C., et al., "Ganglioside alternations in stimulated murine macrophages,"*Biochimica et Biophys. Acta*, 1985, 818, 81-86.

Yohe, H.C., et al., "Ganglioside expression in macrophages from endotoxin responder and nonresponder mice," *J. of Immunol.*, 1986, 137, 3921-3927.

Yohe, H.C., et al., "The presence of sialidase-sensitive sialosylgangliotetraosyl ceramide $G_{M1b}$ in stimulated murine macrophages,"*J. of Immunol.*, 1991, 146, 1900-1908.

Zador, I.Z., et al., "A role for glycosphingolipid accumulation in the renal hypertrophy of steptozotocin-induced diabetes mellitus,"*J. Clin. Invest.*, 1993, 91, 797-803.

Abe et al., Induction of glucosylceramide synthase by synthase inhibitors and ceramide, 333-341, (1996).

Butters et al., Therapeutic applications of imino sugars in lysosomal storage disorders, Current Topics in Medicinal Chemistry, 3, 561-574 (2003).

Carey, Organic Chemistry, $2^{nd}$ Edition, pp. 28-29, 268-271.

Chen et al., Abnormal transport along the lysomal pathway in mucolipidosis, type IV disease, Proc. Natl. Acad. Sci. USA, 95, 6373-6378, (1998).

Greene, Protective groups in organic synthesis, Wiley-Interscience Publication, pp.: cover, 10, 11, 29 (1982).

Mellor, High-performance cation-exchange chromatography and pulsed amperometric detection for the separation, detection, and quantitation of N-alkylated imino sugars in biological samples, Analytical Biochemistry, XP-001055984, 284, 136-142 (2000).

Merzak et al., Gangliosides modulate proliferation, migration, and invasiveness of human brain tumor cells in vitro, Mol. & Chem. Nueuropathology, 24, 121-135 (1995).

Morrison et al., Organic Chemistry, $5^{th}$ Edition, pp. 138-141.

Overkleeft et al., Generation of specific deoxynojirimycin-type inhibitors of the non-lysomal glucosylceramidase, J. of Bio. Chem, 273(41), 26522-26527 (1998).

Platt et al., N-Butyldeoxynojirimycin is a novel inhibitor of glycolipid biosynthesis, 269(11), 8362-8365 (1994).

Schaller et al., Total synthesis of (+)–and (−)- 1-deoxynojirimycin (1,5-dideoxy-1,5-imino-D-and L-glucitol) and of (+)-and (−)-1-deooxyidonojirimycin(1,5-didoxy-1,5-imino-D and L-iditol) via furoisoxazoline-3-aldehydes, Carbohydrate Res., 314, 25-35, (1998).

Schneider, GM1 ganglioside in the treatment of Parkinson's Disease, Ann. NY Acad. Sci., 845, 363-373 (1998).

Tyle, Iontophoretic devices for drug delivery, Pharm. Res., 3, 318-326 (1986).

Van Der Spoel et al., Reversible infertility in male mice after oral administration of alkylated imino sugars: A nonhormonal approach to male contraception, Proc. Natl. Acac. Sci. USA, 99(26), 17173-17178 (2002).

Silva, et al., Advances in Prodrug Design, Mini-Reviews in Medicinal Chemistry, 2005, vol. 5, pp. 893-914.

Wu, W. et al., Synthesis and Biological Activity of a Gemcitabine Phosphoramidate Prodrug, J. Med. Chem., 2007, vol. 50(15); pp. 3743-3746.

Yildiz, Y. et al., Mutation of β-glucosidase 2 causes glycolipid storage disease and impaired male fertility, The Journal of Clinical Investigation, 2006, vol. 116, No. 11, pp. 2985-2994.

Cruz. J.C., et al., Fate of Endogenously Synthesized Cholesterol in Niemann-Pick Type C1 Cells, The Journal of Biological Chemistry, 2000, Issue of Dec. 29, vol. 275, No. 52, pp. 41309-41316.

Liu, Y. et al., Alleviation of neuronal ganglioside storage does not improve the clinical course of the Niemann-Pick C disease mouse, Human Molecular Genetics, 2000, vol. 9., No. 7, pp. 1087-1092.

Platt, F.M. et al., New Therapeutic Prospects for the Glycosphingolipid Lysosomal Storage Diseases, Biochemical Pharmacology, 1998, vol. 56, pp. 421-430.

Zervas, M. et al, Critical role for glycosphingolipids in Niemann-Pick disease type C, Current Biology, 2001, 11, pp. 1283-1287.

Baxter, E.W. et al., "Expeditious Synthesis of Azasugars by the Double Reductive Amination of Dicarbonyl Sugars", Journal of Organic Chemistry, (1994), 59(11), pp. 3175-3185.

Drayer et al., Clinical and Pharmacology and Therapeutics, 1986.

Hutt and O'Grady, Drug Chirality, 1996.

Lin and Lu et al., Role of Pharmacokinetics and Metabolism in Discovery and Development, 1997.

Testa et al., Racemates Versus Enantiomers in Drug Development, 1990.

Asano, K., "New entry for asymmetric deoxyazasugar synthesis: syntheses of deoxymannojirimycin, deoxyaltrojirimycin and deoxygalactostatin", Chem. Commun., 1999, pp. 41-42.

Asano, N. et al., Novel α-L-fucosidase inhibitors from the bark of angylocalyx pynaertii (leguminosae), Eur. J. Biochem., 2001, 268, pp. 35-41.

Barili, P.L. et al., "Double reductive amination of L-arabino-hexos-5-uloses: a diastereoselective approach to 1-deoxy-D-galactostatin derivatives (#)(°)," Tetahedron, 1997, 53(9), pp. 3407-3416.

Baxter, E.W. at al., "Expeditious synthesis of azasugars by the double reductive amination of dicarbonyl sugars", J. Org. Chem., 1994, 59, pp. 3175-3185.

Bernotas, R.C. et al., Efficient preparation of enantiomerically pure cyclic aminoalditols total synthesis of 1-deoxynojirimycin and 1-deoxymannojirimycin, Tetrahedron Letts., 1985, 26(9), 1123-1126.

Fouace, S. et al., Lipophilic prodrugs of 1-deoxynojirimycin derivatives, Tetrahedron Letts., 2000, 41, 7313-7315.

Godskesen, M. et al., Deoxyiminoalditols from aldonolactones—V. preparation of the four stereoisomers of 1,5-dideoxy-1,5-iminopenitols. Evaluation of these iminopentitols and three 1,5-dideoxy-1,5-iminohepitols as glycosidase inhibitors, Bioorganic & Medicinal Chem., 1996, 4(11), pp. 1857-1865.

Grandel, R. et al., A short synthesis of azasugars via aldol reaction of chelated amino acid ester enolates, Tetrahedron Letts., 1997, 38(46), pp. 8009-8012.

Greene et al., Table of Content, Protective Groups in Organic Chemistry, $2_{nd}$ Ed., Wiley-Interscience, NY, 1991.

Hugel, H.M. et al., Stereoselective electrophilic cyclizations of δ-aminoalkenes derived from carbohydrates: synthesis of polyhydroxypiperidines, Aust. J. Chem., 1998, 51, pp. 1149-1155.

Ikota, N. et al., Improved synthesis of 1-deoxynojirimycin and facile synthesis of its stereoisomers from (S)-pyroglutamic acid derivative, Heterocycles, 1997, 46, pp. 637-643.

Kajimoto, T. et al., Palladium-mediated stereocontrolled reductive amination of azido sugars prepared from enzymatic adol condensation: a general approach to the synthesis of deoxy aza sugars, J. Am. Chem. Soc., 1991, 113, pp. 6678-6680.

Kazmaier, U. et al., A short synthesis of polyhydroxylated piperidines by adol reaction of chelated amino acid ester enolates, Eur. J. Org. Chem., 1998, pp. 1833-1840.

Lee, B.W. et al., A short and efficient synthesis of 2R,3R,4R-3,4-dihydroxyproline, 1,4-dideoxy-1,4-imino-L-xylitol, 2R,3R,4R,5S-3,4,5-trihydroxypipecolic acid, and 1,5-dideoxy-1,5-imino-L-iditol, Synthesis, 2000, 9, pp. 1305-1309.

Liotta, L.J. et al., A new class of endoglycosidase inhibitors. Studies on endocellulases, J. Am. Chem. Soc., 1989, III, pp. 783-785.

Lundt, I. et al., Deoxyiminoalditols from aldonolactones; IV: preparation of 1,5-dideoxy-1,5-iminoheptitols with L-glycero-D-manno, D-glycero-L-gulo and L-glycero-D-altro configuration, Synthesis, Jul. 1995, pp. 787-794.

Mehta, G. et al., A norbomyl route to azasugars: a new synthesis of deoxynojirimycin analogues, Tetrahedron Letts., 2000, 41, pp. 5741-5745.

Paulsen, H. et al., Uber monosaccharide mit stickstoffhaltigem siebenring, Chem. Ber., 1967, 100, 512-520 (German language); Chemical Abstracts #3208 Thymine nucleosides of 3-deoxy-d-xylohexose, p. 3207.

Paulsen, H. et al., Synthese and reaktionen von keto-piperidinosen, Chem. Ber., 1967, 100, pp. 802-815 (English Abstract).

Reitz, A.B. et al., Pyrrolidine and piperidine aminosugars from dicarbonyl sugars in one step. Concise synthesis of 1-deoxyojirimycin, Tetrahedron Letts., 1990, 31(47), pp. 6777-6780.

Subramanian, T. et al., Synthesis of oxazolidinyl azacycles via ring-closing olefin metathesis: a practical entry to the synthesis of deoxyazasugars and hydorxypyrrolizidines, Tetrahedron Lettts., 3001, 42, 4079-4082.

Uriel, C. et al., A short and efficient synthesis of 1,5-dideoxy-1,5-imino-D-galactitol (1-deoxy-D-galactostatin) and 1,5-dideoxy-1,5-imino-L-altritol (10deoxy-L-altrostatin) from D-galactose, Synlett, 1999, 5, pp. 593-595.

Xu, Y.-M. et al., A new approach to 1-deoxy-azasugars: asymmetric synthesis of 1-deoxymannojirimycin and 1-deoxyaltronojirimycin, J. Chem. Sco. Perkin Trans., 1997, 1, pp. 741-746.

Actions Related to U.S. Appl. No. 11/196,153.

* cited by examiner

PIPERIDINETRIOL DERIVATIVES AS INHIBITORS OF GLYCOSYLCERAMIDSYNTHASE The present invention relates to novel piperidine derivatives useful as inhibitors of glucosylceramide synthase (GCS; UDP-glucose:ceramide glucosyltransferase, UDP-glucose: N-acylsphingosine D-glucosyltransferase, EC 2.4.1.80), methods for their preparation and their use in medicine, specifically in the treatment and prevention of disease states mediated by GCS. The compounds find use in the treatment of glycolipid storage diseases, diseases associated with glycolipid accumulation, cancers in which glycolipid synthesis is abnormal, infectious diseases caused by organisms which use cell surface glycolipids as receptors, infectious diseases in which synthesis of glucosylceramide is essential or important, diseases in which excessive glycolipid synthesis occurs, neuronal disorders, neuronal injury and inflammatory diseases or disorders associated with macrophage recruitment and activation.

GCS is an intracellular enzyme that catalyzes the assembly of uridine diphosphate-glucose and ceramide into the glycolipid, glucosylceramide. The role of GCS in regulating ceramide levels has been explored, since this molecule can induce apoptotic cell death (J. Biol. Chem., 2000, 275(10), 7138-43). The role of GCS in maintaining cholesterol/glycolipid 'rafts', cell-surface membrane domains of specialized permeability and functionality that appear to be involved in a variety of signal transduction events, has also been investigated (Nature, 1997, 387(6633), 569-72).

GCS is considered to be a target for treating certain human diseases. Glucosylceramide and structurally related glycolipids are stored in the lysosomes of patients with genetic diseases, which result from a mutation in one of the essential glycolipid-degrading enzymes (e.g. Gaucher, Tay Sachs, Sandhoffs, GM1 gangliosidosis and Fabry diseases). Glycolipid storage also occurs as a secondary effect in some tissues (e.g. neuronal tissue) with genetic storage diseases such as Niemann-Pick C disease, mucopolysaccharidoses, mucolipidosis type IV (Proc. Natl. Acad. Sci. USA, 1998, May 26, 95(11), 6373-8) and α-mannosidosis (Proc. Natl. Acad. Sci. USA, 1991, Dec 15, 88(24), 1133-04). GCS inhibitors may be applied to reduce the rate of glycolipid synthesis in diseased cells so that there is less glycolipid present to be stored, a treatment approach termed substrate deprivation. Studies have demonstrated that GCS inhibitors can be used to reduce the glycolipid accumulation seen in cell and animal models of glycolipid storage disorders (Proc. Natl. Acad. Sci. USA, 1999, 96(11), 6388-93; Science, 1997, 276(5311), 428-31; J. Clin. Invest., 2000, 105(11), 1563-71). Furthermore, clinical trials have shown that GCS inhibitors, such as, N-butyldeoxynojirimycin (NB-DNJ) are useful in treating human patients with Gaucher disease (Lancet, 2000, 355(9214), 1481-5). The use of the imino sugar NB-DNJ as a GCS inhibitor is disclosed in EP-A-0698012. EP-A-0536402 and EP-A-0698012 disclose that N-alkyl derivatives of deoxygalactonojirimycin, e.g. N-butyldeoxygalactonojirimycin (NB-DGJ), may also be of use in the treatment of glycolipid storage disorders. EP-A-0698012 also discloses that the corresponding N-butyl derivatives of mannose (NB-DMJ), fucose (NB-DFJ) and N-acetylglucosamine (NB-NAG) do not act as inhibitors of glycolipid biosynthesis.

The use of GCS inhibitors in the treatment of human malignancies has also been proposed. Tumours can synthesize abnormal quantities of glycolipids that are typically present/ absent in normal tissues. In addition glycolipids, or gangliosides, in particular are shed by tumour cells and released into the extracellular space and the bloodstream. Both tumour shed and cell surface bound tumour gangliosides can influence tumour host cell interactions such as cell-cell contacts or adhesion (Methods Enzymol., 2000, 312, 447-58), cell motility (Mol. Chem. Neuropathol., 1995, 24(2-3), 121-35), growth factor signalling events (J. Biol. Chem., 2000, 275 (44), 34213-23), tumour stimulated angiogenesis (Acta. Oncol., 1997, 36(4), 383-7) and tumour specific immune responses (J. Immunol., 1999, Oct 1, 163(7), 3718-26). All these events can affect tumour development and progression. Glycolipids, glucosylceramide in particular, are known to accumulate in multidrug resistant (MDR) tumour cells (Anticancer Res., 1998, 18(1B), 475-80) and in vitro treatment of these cells with GCS inhibitors can reverse the MDR phenotype (J. Biol. Chem., 1997, 272(3), 1682-7; Br. J. Cancer, 1999, 81(3), 423-30).

Cell surface glycolipids also have roles in infectious disease, serving as receptors for the binding of pathogenic bacteria (APMIS, 1990, Dec, 98(12), 1053-60, Review), fungi (Infect. Immun., 1990 July, 58(7), 2085-90) and viruses (FEBS Lett., 1984, May 7, 170(1), 15-18). In addition, glycolipids on the surface of cells are bound by bacterial toxins (Methods Enzymol., 2000, 312, 459-73) for instance, the B subunit of cholera toxin (ganglioside GM1) and verocytotoxin (globotriaosylceramide GB3) (J. Infect. Dis., 2001, suppl. 7073, 183).

GCS inhibitors may also find use in the treatment of viral infections.

The use of GCS inhibitors may also be appropriate in a number of other clinical indications which are associated with abnormalities in glycolipid synthesis. Atherosclerotic lesions of human aorta have a higher ganglioside content than unaffected regions of the aorta and serum ganglioside concentrations in atherosclerotic patients are higher than in normal individuals (Lipids, 1994, 29(1), 1-5). Tissue derived from the kidneys of patients with polycystic kidney disease contains high levels of both glucosylceramide and lactosylceramide (J. Lipid. Res., 1996, Jun, 37(6), 1334-44). Renal hypertrophy in an animal model of diabetes is associated with increases in glycolipid synthesis, (J. Clin. Invest., 1993, Mar, 91(3), 797-803).

Glycolipid metabolism also plays a critical role in neuronal disorders, such as Alzheimer's disease and epilepsy. For instance, Niemann-Pick C(NPC) patient neurons present with fibrillar tangles reminiscent of the morphology seen in Alzheimer's disease.

GM1 ganglioside binding by amyloid beta-protein induces conformational changes that support its formation of fibrous polymers and the fibrillar deposition of this protein is an early event in Alzheimer's disease (Yanagisawa et al., 1995, Nat. Med. 1, 1062-6; Choo-Smith et al., 1997, Biol. Chem., 272, 22987-90). Thus, decreasing GM1 synthesis by using agents such as GCS inhibitors, e.g. NB-DNJ, could inhibit the fibre formation seen in Alzheimer's disease.

In contrast, preliminary clinical trials have shown that neurodegenerative processes seen in Parkinson's disease, stroke and spinal cord injuries seem to improve by treating patients with GM1 ganglioside (Alter, (1998), Ann. NY Acad. Sci., 845, 391-4011; Schneider, 1998, Ann. NY. Acad. Sci., 845, 363-73; Geisler, (1998), Ann. NY. Acad. Sci., 845, 374-81). It is possible that co-administering glucosylceramide synthesis inhibitors would provide the clinician greater control over this treatment course. GCS inhibitors like NB-DNJ would limit patient-specific inconsistencies by blocking their neuronal glycolipid synthesis. In addition, inhibiting glucosylceramide synthesis would limit the metabolism of administered glycolipids into other, perhaps unproductive, forms. Thus, the ability to modulate glucosylceramide synthesis with GCS inhibitors may be useful in the treatment of a wide variety of neuronal disorders.

In addition, it has also been shown that imino sugars can reversibly induce male sterility and can, therefore, be used as male contraceptives. Also, GCS inhibitors could be used for the treatment of obesity.

A role for glycolipids in some aspects of inflammatory or immune responses has also been suggested. Following an inflammatory stimulus, such as that obtained with thioglycolate, the ganglioside profile of murine peritoneal macrophages changes from a simple profile (3 major species) in resting macrophage to a more complex profile (more than 14 species) in activated and recruited macrophage, see Ryan, J. L. et al., Yale J. Biol. Med., 1985, 58(2) 125-31; Yohe, H. C. et al., Biochim Biophys. Acta., 1985, 818(1), 81-6; Yohe, H. C. et al., Immunol., 1991, 146(6), 1900-8. Furthermore, in vivo administration of an inflammatory agent, e.g. bacterial endotoxin, results in the increased expression of two enzymes, serine palmitoyltransferase and glucosylceramide synthase, which are key to the de novo synthesis of glycolipids, see Memon, R. A. et al., J. Biol. Chem., 1999, 274(28), 19707-13; Memon, R. A. et al., J. Lipid. Res., 2001, 42(3), 452-9.

Such a role for glycolipids is further supported by the demonstration of changes in glycolipid expression in animals with genetic defects which result in hyper- or hypo-sensitive responses to inflammatory stimuli. For example, upon endotoxin treatment in C3H/HeJ mice, which have a toll-like receptor 4 mutation and are hypo-responsive to bacterial endotoxin, recruited macrophages were found to lack ganglioside $G_{M1b}$, which is a major ganglioside found in recruited macrophages in normal mice, see Yohe, H. C. et al., Immunol., 1991, 146(6), 1900-8; Yohe, H. C. et al., Immunol., 1986, 137(12), 3921-7.

Hence, GCS inhibitors may be useful in the treatment of inflammatory diseases and other disorders associated with macrophage recruitment and activation, including but not limited to, rheumatoid arthritis, Crohn's disease, asthma and sepsis.

WO02/055498, published after the priority date of the present application, discloses piperidine derivatives useful as GCS inhibitors.

Given the importance of GCS in a wide spectrum of diseases, it is essential that new tools that provide a means for modulating this enzyme's function be developed. Towards this end, we have identified a class of novel compounds that are useful in inhibiting GCS's catalytic activity.

The compounds of the invention may exhibit improved potency and/or selectivity for GCS, relative to non-lysosomal-β-glucocerebrosidase activity, over known hydroxylated piperidine derivatives.

According to the invention there is provided a compound of formula (I) or a pharmaceutically acceptable salt or prodrug thereof:

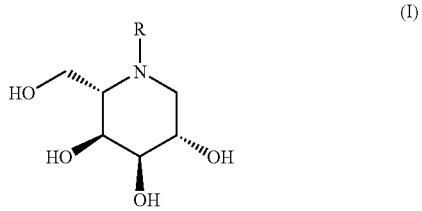

(I)

wherein
R is $C_{1-3}$ alkylAr$^1$ where Ar$^1$ is phenyl or pyridyl;
wherein phenyl is substituted by one or more substituents selected from CN, CON(R$^1$)$_2$, SO$_n$R$^2$, SO$_2$N(R$^1$)$_2$, N(R$^5$)$_2$, N(R$^1$)COR$^2$, N(R$^1$)SO$_n$R$^2$, C$_{0-6}$ alkylAr$^2$, C$_{2-6}$ alkenylAr$^2$ and C$_{3-6}$ alkynylAr$^2$ wherein one or more of the —CH$_2$— groups of the alkyl chain may be replaced with a heteroatom selected from O, S and NR$^3$, provided that when the heteroatom is O, at least two —CH$_2$— groups separate it from any additional O atom in the alkyl chain; or two adjacent substituents on the Ar$^1$ phenyl may together form a fused 5- or 6-membered saturated or unsaturated ring wherein the ring optionally contains 1 or 2 heteroatoms selected from O, S and NR$^4$ and is optionally substituted by one or more substituents selected from, an oxo group, C$_{1-6}$ alkyl and C$_{0-3}$ alkylAr$^4$;

and the Ar$^1$ phenyl is optionally substituted by one or more additional substituents selected from F, Cl, Br, CF$_3$, OCF$_3$, OR$^3$ and C$_{1-6}$ alkyl;

and wherein pyridyl is substituted by one or more substituents, selected from, CN, CON(R$^1$)$_2$, SO$_n$R$^2$, SO$_2$N(R$^1$)$_2$, N(R$^5$)$_2$, N(R$^1$)COR$^2$, N(R$^1$)SO$_n$R$^2$, F, Cl, Br, CF$_3$, OCF$_3$, OR$^3$, C$_{1-6}$ alkyl, C$_{0-6}$ alkylAr$^2$, C$_{2-6}$ alkenylAr$^2$ and C$_{3-6}$ alkynylAr$^2$ wherein one of the —CH$_2$— groups of the alkyl chain may be replaced with a heteroatom selected from O, S and NR$^3$, provided that when the heteroatom is O, at least two —CH$_2$— groups separate it from any additional O atom in the alkyl chain; or two adjacent substituents on the Ar$^1$ pyridyl may together form a fused 5- or 6-membered saturated or unsaturated ring wherein the ring optionally contains 1 or 2 heteroatoms selected from O, S and NR$^4$ and is optionally substituted by one or more substituents selected from, an oxo group, C$_{1-6}$ alkyl and C$_{0-3}$ alkylAr$^4$;

R$^1$ is H, C$_{1-6}$ alkyl optionally substituted by OH, Ar$^3$, or C$_{1-6}$ alkylAr$^3$, or the group N(R$^1$)$_2$ may form a 5- to 10-membered heterocyclic group optionally containing one or more additional heteroatoms selected from O, S and NR$^3$ and is optionally substituted by an oxo group;

R$^2$ is C$_{1-6}$alkyl optionally substituted by OH, Ar$^3$, or C$_{1-6}$ alkylAr$^3$;

R$^3$ is H, or C$_{1-6}$ alkyl;

R$^4$ is H, C$_{1-6}$ alkyl or C$_{0-3}$ alkylAr$^4$;

R$^5$ is H, C$_{1-6}$ alkyl optionally substituted by OH, Ar$^3$ or C$_{1-6}$ alkylAr$^3$, or the group N(R$^5$)$_2$ may form a 5- to 10-membered heterocylic group optionally containing one or more additional heteroatoms selected from O, S and NR$^3$ and is optionally substituted by an oxo group;

Ar$^2$ and Ar$^3$ are independently phenyl or a 5- to 10-membered heteroaryl group containing up to 3 heteroatoms selected from O, S and NR$^3$, which may be optionally substituted by one or more substituents selected from F, Cl, Br, CN, CF$_3$, OCF$_3$, OR$^3$ and C$_{1-6}$ alkyl;

Ar$^4$ is phenyl or pyridyl either of which may be optionally substituted by one or more substituents selected from F, Cl, Br, CN, CF$_3$, OCF$_3$, OR$^3$ and C$_{1-6}$ alkyl; and n is 0, 1 or 2.

R is preferably C$_1$ alkylAr$^1$.

Ar$^1$ is preferably phenyl, wherein phenyl is substituted as defined for formula (I).

Ar$^1$ phenyl is preferably substituted on the para position.

More preferably Ar$^1$ is phenyl, wherein phenyl is substituted by one or more substituents selected from CN, CON(R$^1$)$_2$, SO$_2$N(R$^1$)$_2$, N(R$^5$)$_2$, N(R$^1$)COR$^2$, C$_{0-6}$ alkylAr$^2$ and C$_{2-6}$ alkenylAr$^2$ wherein one or more of the —CH$_2$— groups of the alkyl chain may be replaced with a heteroatom selected from O, S and NR$^3$, provided that when the heteroatom is O, at least two —CH$_2$— groups separate it from any additional O atom in the alkyl chain; or two adjacent substituents on the Ar$^1$ phenyl may together form a fused 5- or 6 membered saturated or unsaturated ring wherein the ring optionally contains 1 or 2 heteroatoms selected from O and NR$^4$ and is optionally substituted by one or more substituents selected from, an oxo group, C$_{1-6}$ alkyl and C$_{0-3}$ alkyl$^4$, and the Ar$^1$ is optionally substituted by one or more additional substituents selected from F, Cl, Br, CF$_3$, OCF$_3$, OR$^3$ and C$_{1-6}$ alkyl.

Yet more preferably Ar$^1$ is phenyl, wherein phenyl is substituted by one or more substituents selected from CN, CON(R$^1$)$_2$, N(R$^5$)$_2$ and C$_{0-6}$ alkylAr$^2$ wherein one or more of the —CH$_2$— groups of the alkyl chain may be replaced with a heteroatom selected from O, S and NR$^3$, provided that when the heteroatom is O, at least two —CH$_2$— groups separate it from any additional O atom in the alkyl chain; or two adjacent substituents on the Ar$^1$ phenyl may together form a fused 5- or 6-membered saturated or unsaturated ring wherein the ring optionally contains 1 or 2 heteroatoms selected from O and NR$^4$ and is optionally substituted by one or more substituents selected from, an oxo group, C$_{1-6}$ alkyl and C$_{0-3}$ alkylAr$^4$, and the Ar$^1$ is optionally substituted by one or more additional substituents selected from F, Cl, Br, CF$_3$, OCF$_3$, OR$^3$ and C$_{1-6}$ allyl.

Even more preferably Ar$^1$ is phenyl, wherein phenyl is substituted by one or more substituents selected from CN, CON(R$^1$)$_2$, N(R$^5$)$_2$ and C$_{0-6}$ alkylAr$^2$ wherein one or more of the —CH$_2$— groups of the alkyl chain may be replaced with O, provided that at least two —CH$_2$— groups separate it from any additional O atom introduced into the alkyl chain, and the Ar$^1$ phenyl is optionally substituted by one or more additional substituents selected from F, Cl, Br, CF$_3$, OCF$_3$, OR$^3$ and C$_{1-6}$ alkyl.

When Ar$^1$ is phenyl and has an additional optional substitutent as defined for formula (I) on the ortho position, the substituent is preferably selected from OCH$_3$ and F. More preferably the ortho substituent is F.

When Ar$^1$ is phenyl substituted by C$_2$ alkylAr$^2$ wherein one of the —CH$_2$— groups of the alkyl chain is replaced with O, preferably, the —CH$_2$— group linked to the Ar$^1$ phenyl is replaced with O.

R$^1$ is preferably H, C$_{1-6}$ alkyl or C$_{1-6}$ alkylAr$^3$. More preferably R$^1$ is H or C$_{1-6}$ alkylAr$^3$.

R$^2$ is preferably Ar$^3$ or C$_{1-6}$ alkylAr$^3$. More preferably R$^2$ is C$_{1-6}$ alkylAr$^3$.

R$^3$ is preferably H.

R$^4$ is preferably H or C$_{1-6}$ alkyl. More preferably R$^4$ is H.

R$^5$ is preferably C$_{1-6}$ alkyl optionally substituted by OH, or C$_{1-6}$ alkylAr$^3$. More preferably R$^5$ is C$_{1-6}$ alkyl.

For the groups R$^1$, R$^2$ or R$^5$, the group C$_{1-6}$ alkylAr$^3$ is preferably C$_{1-3}$ alkylAr$^3$, for example, C$_1$ alkylAr$^3$ or C$_2$ alkylAr$^3$.

Ar$^2$ is preferably phenyl which may be optionally substituted by one or more substituents selected from F, Cl, Br, CN, CF$_3$, OCF$_3$, OR$^3$ and C$_{1-6}$ alkyl.

Ar$^3$ is preferably phenyl which may be optionally substituted by one or more substituents selected from F, Cl, Br, CN, CF$_3$, OCF$_3$, OR$^3$ and C$_{1-6}$ alkyl.

Ar$^4$ is preferably phenyl which may be optionally substituted by one or more substituents selected from F, Cl, Br, CN, CF$_3$, OCF$_3$, OR$^3$ and C$_{1-6}$ alkyl.

n is preferably 2.

In the groups CON(R$^1$)$_2$, SO$_2$N(R$^1$)$_2$, and N(R$^5$)$_2$ the R$^1$ and R$^5$ groups may be the same or different.

When two adjacent substituents on the Ar$^1$ form a fused 5- or 6-membered saturated or unsaturated ring optionally containing 1 or 2 heteroatoms selected from O, S and NR$^4$, examples of bicyclic groups which may be formed include benzofuran, indole, benzoxazine, quinoline and isoquinoline.

When N(R$^1$)$_2$ forms a 5- to 10-membered heterocyclic group optionally containing one or more additional heteroatoms selected from O, S and NR$^3$, examples of heterocyclic groups include, piperidine, piperizine, morpholine and quinoline.

When N(R$^5$)$_2$ forms a 5- to 10 membered heterocyclic group, preferably a 5- or 6-membered heterocyclic group, optionally containing one or more additional heteroatoms selected from O, S and NR$^3$, examples of heterocyclic groups include, piperidine, piperizine and morpholine.

When Ar$^2$ or Ar$^3$ is a 5- to 10-membered heteroaryl group, examples of heteroaryl groups include furan, thiophene, oxazole, triazole, pyridine, pyrazine, pyrimidine, benzofuran benzothiophene and benzoxazine.

A specific group of compounds of formula (I) which may be mentioned are those where R is C$_{1-3}$ alkylaryl where aryl is phenyl or pyridyl;

wherein phenyl is substituted by one or more substituents selected from CN, CON(R$^1$)$_2$, SO$_2$R$^2$, N(R$^2$)$_2$, and N(R$^1$) COR$^2$, or two adjacent substituents on the phenyl may together form a fused 5- or 6-membered saturated or unsaturated ring optionally containing 1 or 2 heteroatoms, selected from N and O, and the phenyl is optionally substituted by one or more additional substituents selected from F, Cl, Br, CF$_3$, OCF$_3$, and OR$^1$;

and wherein pyridyl is substituted by one or more substituents, selected from, CN, CON(R$^1$)$_2$, SO$_2$R$^2$, N(R$^2$)$_2$, N(R$^1$) COR$^2$, F, Cl, Br, CF$_3$, OCF$_3$, and OR$^1$ or two adjacent substituents on the pyridyl may together form a fused 5- or 6-membered saturated or unsaturated ring which may optionally contain 1 or 2 heteroatoms, selected from N and O;

R$^1$ is H, or C$_{1-6}$ alkyl; and

R$^2$ is C$_{1-6}$ alkyl.

Another specific group of compounds of formula (I) that may be mentioned are those where R is C$_{1-3}$ alkylAr$^1$ where Ar$^1$ is phenyl or pyridyl;

wherein phenyl is substituted by one or more substituents selected from CN, CON(R$^1$)$_2$, SO$_2$R$^2$, N(R$^2$)$_2$, N(R$^1$)COR$^2$, and C$_{1-3}$ alkylAr$^2$ wherein one of the —CH$_2$— groups of the alkyl chain may be replaced with O and where Ar$^2$ is phenyl or a 5- or 6-membered heteroaryl group containing up to 3 heteroatoms selected from N, O and S; or two adjacent substituents on the Ar$^1$ phenyl may together form a fused 5- or 6-membered saturated or unsaturated ring optionally containing 1 or 2 heteroatoms selected from N and O;

and wherein pyridyl is substituted by one or more substituents, selected from, CN, CON(R$^1$)$_2$, SO$_2$R$^2$, N(R$^2$)$_2$, N(R$^1$) COR$^2$, F, Cl, Br, CF$_3$, OCF$_3$, OR$^3$, and C$_{1-3}$ allylAr$^2$ wherein one of the —CH$_2$— groups of the alkyl chain may be replaced with O and where Ar$^2$ is phenyl or a 5- or 6-membered heteroaryl group containing up to 3 heteroatoms selected from N, O and S; or two adjacent substituents on the pyridyl may together form a fused 5- or 6-membered saturated or unsaturated ring optionally containing 1 or 2 heteroatoms selected from N and O;

and the Ar$^1$ or Ar$^2$ phenyl is optionally substituted by one or more additional substituents selected from F, Cl, Br, CF$_3$, OCF$_3$, and OR$^3$;

R$^1$ is H, C$_{1-6}$ alkyl, Ar$^3$, or C$_{1-6}$ alkylAr$^3$ where Ar$^3$ is phenyl or a 5- or 6-membered heteroaryl group containing up to 3 heteroatoms selected from N, O and S, any of which may be substituted by one or more substituents selected from F, Cl, Br, CF$_3$, OCF$_3$, and OR$^3$;

R$^2$ is C$_{1-6}$ alkyl, Ar$^3$, or C$_{1-6}$ alkylAr$^3$ where Ar$^3$ is phenyl or a 5- or 6-membered heteroaryl group containing up to 3 heteroatoms selected from N, O and S, any of which may be substituted by one or more substituents selected from F, Cl, Br, CF$_3$, OCF$_3$, and OR$^3$; and R$^3$ is H, or C$_{1-6}$ alkyl.

Yet another specific group of compounds of formula (I) that may be mentioned are those where R is C$_{1-3}$ alkylAr$^1$ where Ar$^1$ is phenyl or pyridyl;

wherein phenyl is substituted by one or more substituents selected from CN, CON(R$^1$)$_2$, SO$_n$R$^2$, SO$_2$N(R$^1$)$_2$, N(R$^2$)$_2$, N(R$^1$)COR$^2$, N(R$^1$)SO$_n$R$^2$, C$_{0-6}$ alkylAr$^2$, C$_{2-6}$ alkenylAr$^2$ and $C_{3-6}$ alkynylAr$^2$ wherein one or more of the —CH$_2$— groups of the alkyl chain may be replaced with a heteroatom selected from O, S and NR$^3$, provided that when the heteroatom is O, at least two —CH$_2$— groups separate it from any additional O atom in the alkyl chain; or two adjacent substituents on the Ar$^1$ phenyl may together form a fused 5- or 6-membered saturated or unsaturated ring wherein the ring optionally contains 1 or 2 heteroatoms selected from O and NR$^4$ and is optionally substituted by one or more substituents selected from, an oxo group, $C_{1-6}$ alkyl and $C_{0-3}$ allkyAr$^4$;

and the Ar$^1$ phenyl is optionally substituted by one or more additional substituents selected from F, Cl, Br, CF$_3$, OCF$_3$, OR$^3$ and $C_{1-6}$ alkyl;

and wherein pyridyl is substituted by one or more substituents, selected from, CN, CON(R$^1$)$_2$, SO$_n$R$^2$, SO$_2$N(R$^1$)$_2$, N(R$^2$)$_2$, N(R$^1$)COR$^2$, N(R$^1$)SO$_n$R$^2$, F, Cl, Br, CF$_3$, OCF$_3$, OR$^3$, $C_{1-6}$ alkyl, $C_{0-6}$ alkylAr$^2$, $C_{2-6}$ alkenylAr$^2$ and $C_{3-6}$ alkynylAr$^2$ wherein one of the —CH$_2$— groups of the alkyl chain may be replaced with a heteroatom selected from O, S and NR$^3$, provided that when the heteroatom is O, at least two —CH$_2$— groups separate it from any additional O atom in the alkyl chain; or two adjacent substituents on the Ar$^1$ pyridyl may together form a fused 5- or 6-membered saturated or unsaturated ring wherein the ring optionally contains 1 or 2 heteroatoms selected from O and NR$^4$ and is optionally substituted by one or more substituents selected from, an oxo group, $C_{1-6}$ alkyl and $C_{0-3}$ alkylAr$^4$;

R$^1$ is H, $C_{1-6}$ alkyl, Ar$^3$, or $C_{1-6}$ alkylAr$^3$, or the group N(R$^1$)$_2$ may form a 5- to 10 membered heterocyclic group optionally containing one or more additional heteroatoms selected from O and NR$^3$;

R$^2$ is $C_{1-6}$ alkyl, Ar$^3$, or $C_{1-6}$ alkylAr$^3$, or the group N(R$^2$)$_2$ may form a 5- to 6-membered heterocylic group optionally containing one or more additional heteroatoms selected from O and NR$^3$ and is optionally substituted by an oxo group;

R$^3$ is H, or $C_{1-6}$ alkyl;

R$^4$ is H, $C_{1-6}$ alkyl or $C_{0-3}$ alkylAr$^4$;

Ar$^2$ is phenyl or a 5- or 6-membered heteroaryl group containing up to 3 heteroatoms selected from O, S and NR$^3$, any of which may be optionally substituted by one or more substituents selected from F, Cl, Br, CN, CF$_3$, OCF$_3$, OR$^3$ and $C_{1-6}$ alkyl;

Ar$^3$ is phenyl or a 5- to 10 membered heteroaryl group containing up to 3 heteroatoms selected from O, S and NR$^3$, any of which may be optionally substituted by one or more substituents selected from F, Cl, Br, CN, CF$_3$, OCF$_3$, OR$^3$ and $C_{1-6}$ alkyl;

Ar$^4$ is phenyl or pyridyl either of which may be optionally substituted by one or more substituents selected from F, Cl, Br, CN, CF$_3$, OCF$_3$, OR$^3$ and $C_{1-6}$ alkyl; and n is 0, 1 or 2.

The compounds of the invention preferably have a molecular weight of less than 800, more preferably less than 600.

The term "alkyl" as used herein whether on its own or as part of a larger group e.g. "alkylaryl", includes both straight and branched chain radicals. The term alkyl also includes those radicals wherein one or more hydrogen atoms are replaced by fluorine. Alkenyl and alkynyl are to be interpreted accordingly.

The term "heterocyclic group" as used herein includes, unless otherwise defined, non-aromatic and aromatic, single and fused, rings containing one or more, e.g. up to three, heteroatoms in each ring, each of which is selected from O, S and N, which rings, may be unsubstituted or substituted. Each heterocyclic ring suitably has from 5 to 10, preferably 5, 6, 9 or 10 ring atoms. A fused heterocyclic ring system may include carbocyclic rings and need include only one heterocyclic ring. Examples of heterocyclyl groups, including heteroaromatic ring systems, are as follows: pyrrolidine, piperidine, piperazine, morpholine, imidazolidine, pyrazolidine, pyrrole, quinoline, isoquinoline, pyridine, pyrazine, pyrimidine, oxazole, thiazole, thiophene, indole, furan, thiadiazole, triazole, imidazole, benzopyran, benzofuran, benzothiophene, benzoxazine and benzamidazole. "Heteroaryl" is to be interpreted accordingly.

Specific compounds of the invention include the compounds provided in the Examples and pharmaceutically acceptable salts and prodrugs thereof.

Preferred compounds of the invention include:
Benzamide, N-[(4-fluorophenyl)methyl]-4-[[(2S,3S,4R,5S)-3,4,5-trihydroxy-2-hydroxymethyl)-1-piperidinyl]methyl]-,
3,4,5-Piperidinetriol, 2-(hydroxymethyl)-1-[[4-(phenylmethoxy)phenyl]methyl]-, (2S,3S,4R,5S),
Benzamide, N-[1-(R)-(phenyl)ethyl]-4-[[(2S,3S,4R,5S)-3,4,5-trihydroxy-2-(hydroxymethyl)-1-piperidinyl]methyl]-;
3,4,5-Piperidinetriol, 1-[(3-cyano-4-dipropylamino)phenyl)methyl]-2-(hydroxoymethyl)-, (2S,3S,4R,5S),
Benzamide, N-[1-(S)-4-fluorophenyl)ethyl]-4-[[(2S,3S,4R,5S)-3,4,5-trihydroxy-2-(hydroxymethyl)-1-piperidinyl]methyl]-,
Benzamide, N-[1-(R)-(4-fluorophenyl)ethyl]4-[[(2S,3S,4R,5S)-3,4,5-trihydroxy-2-(hydroxymethyl)-1-piperidinyl]methyl]-;
3,4,5-Piperidinetriol, 2-(hydroxymethyl)-1-[(2-phenyl-2H-1,4-benzoxazin-3(4H)-one-6-yl)methyl]-, (2S,3S,4R,5S) and pharmaceutically acceptable salts and prodrugs thereof.

A highly preferred compound of the invention is:
3,4,5-Piperidinetriol, 2-hydroxymethyl)-1-[[4-(phenylmethoxy)phenyl]methyl]-, (2S,3S,4R,5S) and pharmaceutically acceptable salts and prodrugs thereof.

As described herein, for all aspects of the invention, reference to compounds of formula (I) encompasses pharmaceutically acceptable salts and prodrugs thereof.

As described herein, the compounds of the present invention can be used for the inhibition of GCS. Thus, an aspect of the present invention provides the use of the compounds of formula (I) in medicine.

Suitable, pharmaceutically acceptable salts of the compounds of formula (I) include, but are not limited to, salts with inorganic acids such as hydrochloride, sulfate, phosphate, diphosphate, hydrobromide and nitrate, or salts with an organic acid such as malate, maleate, fumarate, tartrate, succinate, citrate, acetate, lactate, methanesulfonate, p-toluenesulfonate, palmitate, salicylate and stearate.

Suitable prodrugs of the compounds of formula (I) include, but are not limited to, pharmaceutically acceptable esters such as $C_{1-6}$ alkyl esters.

Some of the compounds of this invention may be crystallised or recrystallised from solvents such as aqueous and organic solvents. In such cases solvates may be formed. This invention includes within its scope stoichiometric solvates including hydrates as well as compounds containing variable amounts of water that may be produced by processes such as lyophilisation.

Certain of the R groups of compounds of formula (I) may exist in the form of optical isomers, e.g. diastereoisomers and mixtures of isomers in all ratios, e.g. racemic mixtures. The invention includes all such forms, in particular the pure isomeric forms. The different isomeric forms may be separated or resolved one from the other by conventional methods, or any given isomer may be obtained by conventional synthetic methods or by stereospecific or asymmetric syntheses.

The compounds of the invention may exist as tautomers, e.g. keto/enol tautomers, all of which are included within the scope of formula (I).

Since the compounds of formula (I) are intended for use in pharmaceutical compositions it will readily be understood that they are preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions; these less pure preparations of the compounds should contain at least 1%, more suitably at least 5%, e.g. 10 to 59%, of a compound of formula (I) or pharmaceutically acceptable derivative thereof.

The compounds of formula (I) can be prepared by art-recognized procedures from known or commercially available starting materials. If the starting materials are unavailable from a commercial source, their synthesis is described herein, or they can be prepared by procedures known in the art.

Specifically, the compounds of formula (I) may be prepared by processes comprising:

a) reductive amination of an aldehyde of formula $R^5CHO$ wherein $R^5$ is $C_{0-2}$ alkylAr$^1$ where Ar$^1$ is as defined in formula (I) with a compound of formula (II):

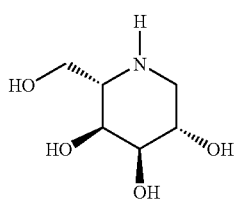

(II)

the reductive amination may be perfomed by methods known to those skilled in the art, e.g. using NaBH3CN or a supported reagent such as (polystyrylmethyl) trimethylammonium cyanoborohydride in acetic acid-methanol or HCl-methanol, or using NaBH(OAc)$_3$ in a solvent, such as dichloromethane; or b) deprotection of a compound of formula (III):

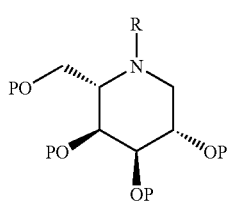

(III)

wherein R is as defined in formula (I) and P, which may be the same or different, are hydroxy protecting groups e.g. benzyl or substituted benzyl. When P is benzyl or substituted benzyl the deprotection is preferably conducted in the presence of hydrogen gas and a catalyst, such as, PdCl$_2$ or palladium on carbon in a suitable solvent, such as, an alcohol, e.g. ethanol. It will be understood that when P is benzyl or substituted benzyl and R is substituted benzyl, the R group can also be removed under these conditions to give compounds of formula (II). Thus, compounds of formula (I) where R is substituted benzyl are preferably produced using process a) above.

The compound of formula (II) is known, see e.g. Tet. Lett., 1997, 38(45), 8009-12.

Compounds of formula (III) may be prepared by reacting a compound of formula (IV):

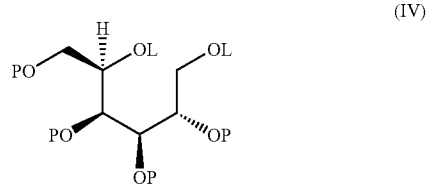

(IV)

wherein OL, which may be the same or different are leaving groups, such as mesyloxy, and P is as defined for formula (III), with an amine of formula RNH$_2$, wherein R is as defined in formula (I), either neat or in a solvent such as tetrahydrofuran.

Compound (IVa), wherein L is mesyl and P is benzyl, may be prepared by reacting 2,3,4,6-tetra-O-benzyl-D-galactitol with mesyl chloride in the presence of a base such as pyridine, as described in WO02/055498.

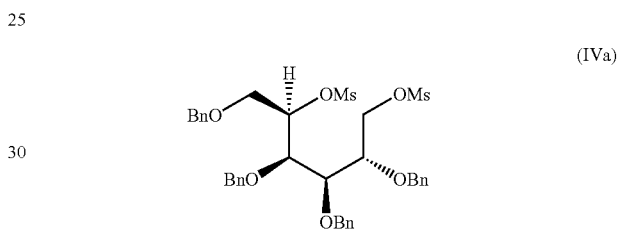

(IVa)

Any novel intermediate compounds as described herein also fall within the scope of the present invention. Thus according to a further aspect of the invention there is provided a compound of formula (III) as defined above.

The invention also provides a compound of formula (I) when produced according to the methods described above.

During the synthesis of the compounds of formula (I) labile functional groups in the intermediate compounds, e.g. hydroxy, carboxy and amino groups, may be protected. A comprehensive discussion of the ways in which various labile functional groups may be protected and methods for cleaving the resulting protected derivatives is given in for example *Protective Groups in Organic Chemistry*, T. W. Greene and P. G. M. Wuts, (Wiley-Interscience, New York, 2nd edition, 1991).

The compounds of formula (I) may be prepared singly or as compound libraries comprising at least 2, for example 5 to 500 compounds and more preferably 10 to 100 compounds of formula (I). Libraries of compounds of formula (I) may be prepared by multiple parallel synthesis using either solution phase or solid phase chemistry, by procedures known to those skilled in the art.

Thus according to a further aspect of the invention there is provided a compound library comprising at least 2 compounds of formula (I) or pharmaceutically acceptable salts or prodrugs thereof.

The pharmaceutically acceptable salts and prodrugs of the compounds of formula (I) may be prepared by methods well known to those skilled in the art.

The pharmaceutically effective compounds of formula (I) may be administered in conventional dosage forms prepared by combining a compound of formula (I) ("active ingredient") with standard pharmaceutical carriers, excipients or diluents according to conventional procedures well known in the art. These procedures may involve mixing, granulating and compressing or dissolving the ingredients as appropriate to the desired preparation.

According to a further aspect, the present invention provides a pharmaceutical composition comprising a compound of formula (I), together with one or more pharmaceutically acceptable carriers, excipients and/or diluents.

The active ingredient or pharmaceutical composition can be administered simultaneously, separately or sequentially with another treatment for the disorder to be treated.

The active ingredient or pharmaceutical composition may be administered to a subject by any of the routes conventionally used for drug administration, for example they may be adapted for oral (including buccal, sublingual), topical (including transdermal), nasal (including inhalation), rectal, vaginal or parenteral (including subcutaneous, intramuscular, intravenous or intradermal) administration to mammals including humans. The most suitable route for administration in any given case will depend on the particular compound or pharmaceutical composition, the subject and the nature and severity of the disease and the physical condition of the subject. Such compositions may be prepared by any method known in the art of pharmacy, for example by bringing into association the active ingredient with the carrier(s), excipient(s) and/or diluent(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Tablets and capsules for oral administration may be in unit dose presentation form and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulfate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Pharmaceutical compositions adapted for topical administration may be formulated as ointments, creams, suspensions, lotions, powders, solutions, pastes, gels, impregnated dressings, sprays, aerosols or oils and may contain appropriate conventional additives such as preservatives, solvents to assist drug penetration and emollients in ointments and creams. Such applications include those to the eye or other external tissues, for example the mouth and skin and the compositions are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. The composition may also contain compatible conventional carriers, such as cream or ointment bases and ethanol or oleyl alcohol for lotions.

Pharmaceutical compositions adapted for topical administration to the eye include eye drops wherein the active ingredient is dissolved or suspended in a suitable carrier, especially an aqueous solvent.

Pharmaceutical compositions adapted for topical administration in the mouth include lozenges, pastilles and mouth washes.

Pharmaceutical compositions adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318, (1986).

Pharmaceutical compositions adapted for nasal administration wherein the carrier is a solid include a coarse powder having a particle size for example in the range 20 to 500 microns which is administered by rapid inhalation through the nasal passage from a container of the powder held close up to the nose. Suitable compositions wherein the carrier is a liquid, for administration as a nasal spray or as nasal drops, include aqueous or oil solutions of the active ingredient.

Pharmaceutical compositions adapted for administration by inhalation include fine particle dusts or mists which may be generated by means of various types of metered dose pressurised aerosols, nebulizers or insufflators.

Pharmaceutical compositions adapted for rectal administration may be presented as suppositories or enemas. Suppositories will contain conventional suppository bases, e.g. cocoa-butter or other glyceride;

Pharmaceutical compositions adapted for vaginal administration may be presented as pessaries, tampons, creams; gels, pastes, foams or spray compositions.

Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The compositions may be presented in unit-dose or multi-dose containers, for example sealed ampoules and vials and may be stored in a freeze-dried (lyophilieed) condition requiring only the addition of the sterile liquid carrier, for example water for injections, immediately prior to use. Extemporaneous injection solutions and suspensions may be prepared from sterile powders, granules and tablets.

For parenteral administration, fluid unit dosage forms are prepared utilizing the active ingredient and a sterile vehicle, e.g. water. The active ingredient, depending on the vehicle and concentration used, can be either suspended or dissolved in the vehicle. In preparing solutions the active ingredient can be dissolved in water for injection and filter sterilised before filling into a suitable vial or ampoule and sealing.

Advantageously, agents such as a local anaesthetic, preservative and buffering agents can be dissolved in the vehicle. To enhance stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the active ingredient is suspended in the vehicle instead of being dissolved and sterilization cannot be accomplished by filtration. The active ingredient can be sterilised by exposure to ethylene oxide before suspending in the sterile vehicle.

Advantageously, a surfactant or wetting agent is included in the composition to facilitate uniform distribution of the active ingredient.

The pharmaceutical compositions according to the invention are preferably adapted for oral administration.

It should be understood that in addition to the ingredients particularly mentioned above, the compositions may also include other agents conventional in the art having regard to the type of formulation in question, for example those suitable for oral administration may include flavouring agents. They may also contain therapeutically active agents in addition to the compounds of the present invention. Such carriers may be present as from about 1% up to about 98% of the formulation. More usually they will form up to about 80% of the formulation.

The compositions may contain from 0.1% by weight, e.g. 10-60% by weight, of the active material, depending on the method of administration.

Pharmaceutical compositions may be presented in unit dose forms containing a predetermined amount of active ingredient per dose. Such a unit may contain for example 0.1 mg/kg to 750 mg/kg, more preferably 0.1 mg/kg to 10 mg/kg depending on the condition being treated, the route of administration and the age, weight and condition of the patient. Preferred unit dosage compositions are those containing a daily dose or sub-dose, or an appropriate fraction thereof, of an active ingredient.

It will be recognized by one of skill in the art that the optimal quantity and spacing of individual dosages of active ingredients will be determined by the nature and extent of the condition being treated, the form, route and site of administration and the particular subject being treated and that such optimums can be determined by conventional techniques. It will also be appreciated by one of skill in the art that the optimal course of treatment, i.e. the number of doses of the active ingredients given per day for a defined number of days, can be ascertained by those skilled in the art using conventional course of treatment determination tests.

No toxicological effects are indicated when the compounds of formula (I) are administered in the above mentioned dosage range.

The compounds of the invention are useful in that they are capable of inhibiting glucosylceramide synthase. Thus, the compounds of the invention can be used in the treatment of various glycolipid storage diseases, such as, Gaucher's disease, Sandhoffs disease, Tay-Sachs disease, Fabry disease, GM1 gangliosidosis etc. In addition, compounds, such as, this also can find use in the treatment of conditions in which glycolipid accumulation occurs, such as, Niemann-Pick disease, mucopolysaccharidoses (MPS I, MPS IIIA, MPS IIIB, MPS VI and MPS VII, preferably MPS I), mucolipidosis type IV and α-mannosidosis.

The compounds of the present invention can also be used in the treatment of cancers in which glycolipid synthesis is abnormal, such as, brain tumours, neuroblastoma, malignant melanoma, renal adenocarcinoma and multi-drug resistant cancers in general.

The compounds of the present invention can also be used in the treatment of diseases caused by infectious organisms which use cell surface glycolipids as receptors for either the infectious organism itself or for a toxin produced by the infectious organism (e.g. for attachment and/or invasion onto/into the host cell).

The compounds of the present invention may also be used in the treatment of diseases caused by infectious organisms for which the synthesis of glucosylceramide is an essential or important process, such as, pathogenic fungi, e.g. *Cryptococcus neoformans* or viral infections, e.g. viruses that require host cell enzymes to synthesize and properly fold their viral envelope glycoproteins, or viruses that acquire a component of their envelope from an internal host cell membrane. GCS inhibition may result in improper glycoprocessing or the misfolding of one or more viral envelope glycoproteins, inhibition of viral secretion, or improper viral fusion of the virus with its target cells. Suitable viral infections for treatment may be caused by, for example but not limited to, the following viruses: flaviviruses and pestiviruses, e.g. hepatitis C virus, yellow fever virus, dengue viruses 1-4, Japanese encephalitis virus, Murray Valley encephalitis virus, Rocio virus, West Nile fever virus, St. Louis encephalitis virus, tick-borne encephalitis virus, Louping ill virus, Powassan virus, Omsk hemorrhagic fever virus, and Kyasanur forest disease virus; hepadnavirus, e.g. hepatitis B virus; paramyxovirus, e.g. respiratory syncytial virus or retroviruses, such as, human immunodeficiency virus.

The compounds of the present invention can also be used in the treatment of diseases in which excessive glycolipid synthesis occurs, such as, but not limited to, atherosclerosis, polycystic kidney disease and diabetic renal hypertrophy.

The compounds of the present invention can also be used in the treatment of neuronal disorders, such as, Alzheimer's disease or epilepsy; and neuronal degenerative diseases, such as, Parkinsons' disease.

The compounds of the present invention can also be used in the treatment of neuronal injury, such as, spinal cord injuries or stroke.

The compounds of the present invention can also be used for reversibly rendering a male mammal infertile.

The compounds of the present invention can also be used in the treatment of obesity.

The compounds of the present invention can also be used in the treatment of inflammatory diseases or disorders associated with macrophage recruitment and activation, including but not limited to, rheumatoid arthritis, Crohn's disease, asthma and sepsis.

In additional aspects, therefore, the present invention provides:

(i) the use of a compound of formula (I) in the manufacture of a medicament for use as an inhibitor of glucosylceramide synthase.

(ii) the use of a compound of formula (I) in the manufacture of a medicament for the treatment of a glycolipid storage disease. Examples of glycolipid storage disease which can be treated include, but are not limited to, Gaucher disease, Sandhoffs disease, Tay-Sachs disease, Fabry disease or GM1 gangliosidosis.

(iii) the use of a compound of formula (I) in the manufacture of a medicament for the treatment of Niemann-Pick disease, types A and C.

(iv) the use of a compound of formula (I) in the manufacture of a medicament for the treatment of mucopolysaccharidosis type I, mucopolysaccharidosis type IIA, mucopolysaccharidosis type IIIB, mucopolysaccharidosis type VI or mucopolysaccharidosis type VII. Preferably the compounds are used in the treatment of mucopolysaccharidosis type I.

(v) the use of a compound of formula (I) in the manufacture of a medicament for the treatment of α-mannosidosis or mucolipidosis type IV.

(vi) the use of a compound of formula (I) in the manufacture of a medicament for the treatment of cancer in which glycolipid synthesis is abnormal, including but not limited to brain cancer, neuronal cancer, neuroblastoma, renal adenocarcinoma, malignant melanoma, multiple myeloma and multi-drug resistant cancers.

(vii) the use of a compound of formula (I) in the manufacture of a medicament for use in the treatment of Alzheimer's disease, epilepsy or stroke.

(viii) the use of a compound of formula (a) in the manufacture of a medicament for use in the treatment of Parkinson's disease.

(ix) the use of the compound of formula (I) in the manufacture of a medicament in the treatment of spinal injury.

(x) the use of a compound of formula (I) in the manufacture of a medicament for use in the treatment of diseases caused by infectious microorganisms which utilize glycolipids on the surface of cells as receptors for either the organism itself or for toxins produced by the organism.

(xi) the use of a compound of formula (I) in the manufacture of a medicament for use in the treatment of disease caused by infectious organisms for which the synthesis of glucosylceramide is an essential or important process, such as but not limited to, pathologies associated with infections of pathogenic fungi, e.g. *Cryptococcus neoformans* or pathologies associated with viral infections.

(xii) the use of a compound of formula (I) in the manufacture of a medicament for use in the treatment of diseases associated with abnormal glycolipid synthesis, including but not limited to, polycystic kidney disease, diabetic renal hypertrophy and atherosclerosis.

(xiii) the use of a compound of formula (I) in the manufacture of a medicament for the treatment of a condition treatable by the administration of a ganglioside, such as GM1 ganglioside. Examples of such conditions are Parkinson's disease, stroke and spinal cord injuries.

(xiv) the use of a compound of formula (I) in the manufacture of a medicament for reversibly rendering a male mammal infertile.

(xv) the use of a compound of formula (I) in the manufacture of a medicament for the treatment of obesity, e.g. as an appetite suppressant.

(xvi) the use of a compound of formula (I) in the manufacture of a medicament for the treatment of inflammatory diseases or disorders associated with macrophage recruitment and activation, including but not limited to, rheumatoid arthritis, Crohn's disease, asthma and sepsis.

(xvii) a method for the treatment of a glycolipid storage disease, e.g. Gaucher's disease, Sandhoffs disease, Tay-Sachs disease or GM1 gangliosidosis, which comprises the step of administering to a patient an effective amount of a compound of formula (I).

(xviii) a method for the treatment of Niemann-Pick disease, types A and C, which comprises the step of administering to a patient an effective amount of a compound of formula (I).

(xix) a method for the treatment of mucopolysaccharidosis type I, mucopolysaccharidosis type IIIA, mucopolysaccharidosis type IIIB, mucopolysaccharidosis type VI or mucopolysaccharidosis type VII which comprises the step of administering to a patient an effective amount of a compound of formula (I).

(xx) a method for the treatment of α-mannosidosis or mucolipidosis type IV which comprises the step of administering to a patient an effective amount of a compound of formula (I).

(xxi) a method for the treatment of cancer in which glycolipid synthesis is abnormal, including but not limited to brain cancer, neuronal cancer, renal adenocarcinoma, malignant melanoma, multiple myeloma and multi-drug resistant cancers, which comprises the step of administering to a patient an effective amount of a compound of formula (I).

(xxii) a method for the treatment of Alzheimer's disease, epilepsy or stroke which comprises the(step of administering to a patient an effective amount of a compound of formula (I).

(xxiii) a method for the treatment of Parkinson's disease, which comprises the step of administering to a patient an effective amount of a compound of formula (I).

(xxiv) a method for the treatment of spinal injury which comprises the step of administering to a patient an effective amount of a compound of formula (I).

(xxv) a method for the treatment of diseases caused by infectious microorganisms, which utilize glycolipids on the surface of cells as receptors for either the organism itself or for toxins produced by the organism, which comprises the step of administering to a patient an effective amount of a compound of formula (I).

(xxvi) a method for the treatment of diseases caused by infectious organisms, e.g. pathogenic fungi or viruses, for which the synthesis of glucosylceramide is an essential or important process, such as but not limited to, pathologies associated with *Cryptococcus neoformans* infection, or pathologies associated with viral infections, which comprises the step of administering to a patient an effective amount of a compound of formula (I).

(xxvii) a method for the treatment of diseases associated with abnormal glycolipid synthesis including but not limited to polycystic kidney disease, diabetic renal hypertrophy and atherosclerosis, which comprises the step of administering to a patient an effective amount of a compound of formula (I).

(xxviii) a method for the treatment of a condition treatable by the administration of a ganglioside, such as GM1 ganglioside, which comprises the step of administering to a patient an effective amount of a compound of formula (I). Examples of such conditions are, Parkinson's disease, stroke and spinal cord injuries.

(xxix) a method for reversibly rendering a male mammal infertile, which comprises the step of administering to said male mammal an effective amount of a compound of formula (I).

(xxx) a method for the treatment of obesity, which comprises the step of administering to a patient an effective amount of a compound of formula (I).

(xxxi) a method for the treatment of inflammatory diseases or disorders associated with macrophage recruitment and activation, including but not limited to, rheumatoid arthritis, Crohn's disease, asthma and sepsis; which comprises the step of administering to a patient an effective amount of a compound of formula (I).

The invention also provides for the use of a compound of formula (I) for the treatment of the above mentioned diseases and conditions.

All publications, including, but not limited to, patents and patent applications, cited in this specification, are herein incorporated by reference as if each individual publication were specifically and individually indicated to be incorporated by reference herein as though fully set forth.

The invention will now be described by reference to the following examples, which are merely illustrative and are not to be construed as a limitation of the scope of the present invention.

EXAMPLES

Example 1

Benzamide, N-[(4-fluorophenyl)methyl]4-[[(2S,3S,4R,5S)-3,4,5-trihydroxy-2-(hydroxymethyl)-1-piperidinyl]methyl]-,

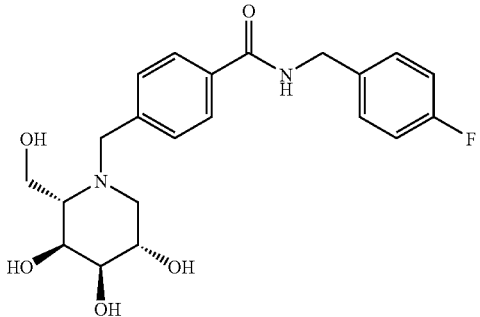

To a mixture of 3,4,5-piperidinetriol, 2(hydroxymethyl)-, (2S,3S,4R,5S) (50 mg, 0.31 mmol) and (polystyrylmethyl) trimethylammonium cyanoborohydride (178 mg, 0.76 mmol) in 10% acetic acid in methanol (2 ml) was added N-[(4-fluorophenyl)methyl]-4-formylbenzamide (196 mg, 0.76 mmol) and the reaction mixture was stirred at room temperature overnight. The reaction mixture was purified using a plug of acidic Dowex 50WX-12 resin (3 g), which had been pre-washed with 10% aqueous hydrochloric acid. The resin was eluted with methanol (25 ml) to remove all non-basic side products. The desired compound was eluted using a solution of 2:2:1 methanol/water/ammonium hydroxide (100 ml). The resulting solution was concentrated to a small volume (1 ml) and freeze dried to afford the title compound as a white solid (70 mg, 57%). $^1$H NMR (d4-methanol) δ 2.52 (1H, m), 2.65 (1H, m), 2.78 (1H, m), 3.60-4.16 (7H, m), 4.5-4.7 (2H, m), 7.06 (2H, m), 7.38 (2H, m), 7.52 (2H, d, J=8 Hz), 7.82 (2H, d, J=8 Hz). MS m/z 404.9 (M)$^+$.

Example 2

3,4,5-Piperidinetriol, 2-(hydroxymethyl)-1-[[4-(phenylmethoxy)phenyl]methyl]-, (2S,3S,4R,5S)

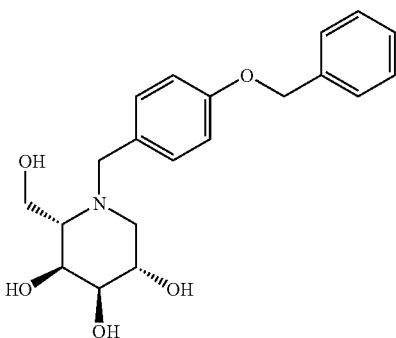

To a mixture of 3,4,5-piperidinetriol, 2-hydroxymethyl)-(2S,3S,4R,5S) (50 mg, 0.31 mmol) and (polystyrylmethyl) trimethylammonium cyanoborohydride (178 mg, 0.76 mmol) in 10% acetic acid in methanol (2 ml) was added (4-phenylmethoxy)benzaldehyde (162 mg, 0.76 mmol) and the reaction mixture was stirred at room temperature overnight. The reaction mixture was purified using a plug of acidic Dowex 50WX-12 resin (3 g), which had been pre-washed with 10% aqueous hydrochloric acid. The resin was eluted with methanol (25 ml) to remove all non-basic side products. The desired compound was eluted using a solution of 2:2:1 methanol/water/ammonium hydroxide (100 ml). The resulting solution was concentrated to a small volume (1 ml) and freeze dried to afford the title compound as a white solid (30 mg, 27%). $^1$H NMR (d4-methanol) δ 2.52 (1H, m), 2.64 (1H, m), 2.75 (1H, m), 3.53-4.0 (7H, m), 5.15 (2H, s), 6.95 (2H, d, J=8.3 Hz), 7.25-7.48 (7H, m). MS m/z 360.0 (M+H)$^+$.

Example 3

Benzamide, N-[1-(S)-(phenyl)ethyl]-4-[[(2S,3S,4R,5S)-3,4,5-trihydroxy-2-(hydroxymethyl)-1-piperidinyl]methyl]-,

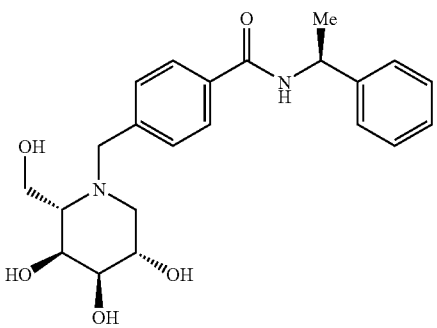

To a mixture of 3,4,5-piperidinetriol, 2-(hydroxymethyl)-, (2S,3S,4R,5S) (50 mg, 0.31 mmol) and (polystyrylmethyl) trimethylammonium cyanoborohydride (178 mg, 0.76 mmol) in 10% acetic acid in methanol (2 ml) was added N-[1-S)-phenyl)ethyl]-4-formylbenzamide (193 mg, 0.76 mmol) and the reaction mixture was stirred at room temperature overnight. The reaction mixture was purified using a plug of acidic Dowex 50WX-12 resin (3 g), which had been pre-washed with 10% aqueous hydrochloric acid. The resin was eluted with methanol (25 ml) to remove all non-basic side products. The desired compound was eluted using a solution of 2:2:1 methanol/water/ammonium hydroxide (100 ml). The resulting solution was concentrated to a small volume (1 ml) and freeze dried to afford the title compound as a white solid (10 mg, 8%). $^1$H NMR (d4-methanol) δ 1.51 (3H, d, J=7.1 Hz), 2.53 (1H, dd, J=6.8 and 12.1 Hz), 2.66 (1H, dd, J=3.8 and 12.1 Hz), 2.79 (1H, m), 3.62-4.00 (6H, m), 4.13 (1H, d, J=13.6 Hz), 5.25 (1H, m), 7.24 (1H, t, J=7.2 Hz), 7.3-7.4 (4H, m), 7.52 (2H, d, J=8.3 Hz), 7.81 (2H, d, J=8.3 Hz). MS m/z 401.0 (M+1)$^+$.

Example 4

3,4,5-Piperidinetriol, 1-[(3-cyano-4-(dipropylamino)phenyl)methyl]-2-(hydroxymethyl), (2S,3S,4R,5S)

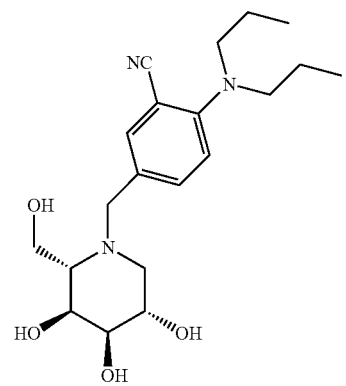

To a mixture of 3,4,5-piperidinetriol, 2-hydroxymethyl)-, (2S,3S,4R,5S) (50 mg, 0.31 mmol) and (polystyrylmethyl) trimethylammonium cyanoborohydride (178 mg, 0.76 mmol) in 10% acetic acid in methanol (2 ml) was added 3-cyano-4-(dipropylamino)benzaldehyde (162 mg, 0.76 mmol) and the reaction mixture was stirred at room temperature overnight. The reaction mixture was purified using a plug of acidic Dowex 50WX-12 resin (3 g), which had been pre-washed with 10% aqueous hydrochloric acid. The resin was eluted with methanol (25 ml) to remove all non-basic side products. The desired compound was then eluted using a solution of 2:2:1 methanol/water/ammonium hydroxide (100 ml). The resulting solution was concentrated to a small volume (1 ml) and freeze dried to afford the title compound as a white solid (30 mg, 27%). $^1$H NMR (d4-methanol) δ 0.93 (6H, t, J=7.3 Hz), 1.6 (4H, m), 2.5-2.85 (3H, m), 3.34 (4H, m), 3.55-4.05 (7H, m), 7.03 (1H, d, J=9 Hz), 7.5 (1H, dd, J=1.9 and 9 Hz), 7.61 (1H, d, J=1.9 Hz). MS m/z 378.1 (M+H)$^+$.

Example 5

Benzamide, N-[1-(S)-(4-fluorophenyl)ethyl]-4-[[(2S,3S,4R,5S)-3,4,5-trihydroxy-2-(hydroxymethyl)-1-piperidinyl]methyl]-,

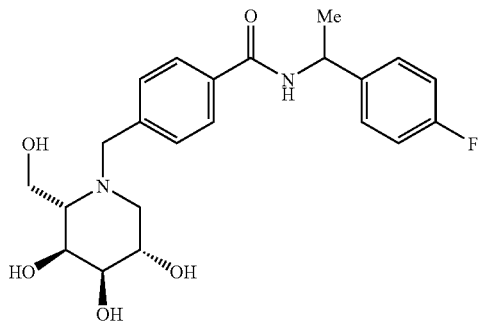

To a mixture of 3,4,5-piperidinetriol, 2-(hydroxymethyl)-, (2S,3S,4R,5S) (50 mg, 0.31 mmol) and (polystyrylmethyl) trimethylammonium cyanoborohydride (178 mg, 0.76 mmol) in 10% acetic acid in methanol (2 ml) was added N-[1S)-(4-fluorophenyl)ethyl]-4-formylbenzamide (207 mg, 0.76 mmol) and the reaction mixture was stirred at room temperature overnight. The reaction mixture was purified using a plug of acidic Dowex 50WX-12 resin (3 g), which had been pre-washed with 10% aqueous hydrochloric acid. The resin was eluted with methanol (25 ml) to remove all non-basic side products. The desired compound was then eluted using a solution of 2:2:1 methanol/water/ammonium hydroxide (100 ml). The resulting solution was concentrated to a small volume (1 ml) and freeze dried to afford the title compound as a white solid, 30 mg (24%). $^1$H NMR (d4-methanol) δ 1.57 (3H, d, J=6.8 Hz), 2.54 (1H, dd, J=6.4 and 12.1 Hz), 2.65 (1H, dd, J=3.8 and 12.1 Hz), 2.79 (1H, m), 3.6-3.98 (6H, m), 4.12 (1H, d, J=14 Hz), 5.23 (1H, q, J=7.2 Hz), 7.06 (2H, m), 7.43 (2H, m), 7.52 (2H, d, J=8.3 Hz), 7.81 (2H, d, J=8.3 Hz). MS m/z 419.0 (M+H)$^+$.

Example 6

Benzamide, N-[1-(R)-(phenyl)ethyl]4-[[(2S,3S,4R,5S)-3,4,5-trihydroxy-2-(hydroxymethyl)-1-piperidinyl]methyl]-,

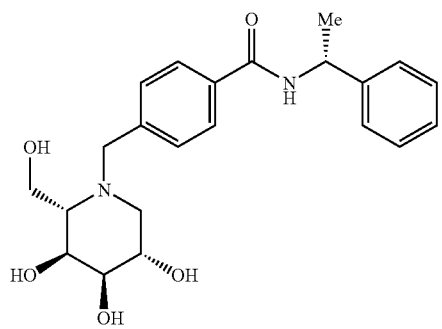

To a mixture of 3,4,5-piperidinetriol, 2-(hydroxymethyl)-, (2S,3S,4R,5S) (150 mg, 0.92 mmol) and (polystyrylmethyl) trimethylammonium cyanoborohydride (540 mg, 2.3 mmol) in methanol (5 ml) was added N-[1-(R)-phenyl)ethyl]-4-formylbenzamide (910 mg, 3.59 mmol). Dichloromethane (1 ml) was added to dissolve the aldehyde and the mixture warmed to dissolve the amine. Acetic acid (0.1 ml, 1.75 mmol) was added to the reaction mixture which was then stirred at room temperature overnight. The reaction mixture was purified using a plug of acidic Dowex 50WX-12 resin (5 g) (which had been pre-washed with 10% aqueous hydrochloric acid, water and then methanol). The resin was eluted with methanol (25 ml) to remove all non-basic side products. The desired compound was then eluted using a solution of 4:1 methanol/ammonium hydroxide (50 nm), then 3:1:1 methanol/dichloromethane/ammonium hydroxide (50 ml). The resulting solution was concentrated to give a gum which was dissolved in hot water, cooled and freeze dried to afford the title compound as a white solid (300 mg 81%). $^1$H NMR (d4-methanol) δ 1.56 (3H, d, J=7.0 Hz), 2.51 (1H, dd, J=6.8 and 12.0 Hz), 2.64 (1H, dd, J=3.8 and 12.0 Hz), 2.77 (1H, ddd, J=4.5, 5.3 and 6.0 Hz), 3.64 (1H, dd, J=3.4 and 6.4 Hz), 3.67 (1H, d, J=13.9 Hz), 3.73 (1H, ddd, J=3.8, 6.4 and 6.8 Hz), 3.83 (1H, dd, J=5.3 and 11.7 Hz), 3.91 (1H, dd, J=4.5 and 11.7 Hz), 3.96 (1H, dd, J=3.4 and 6.0 Hz), 4.12 (1H, d, J=13.9 Hz), 5.24 (1H, q, J=7.0 Hz), 7.22 (1H, t, J=7.2 Hz), 7.32 (2H, t, J=7.2 Hz), 7.39 (2H, d=7.2 Hz), 7.50 (2H, d, J=8.3 Hz), 7.80 (2H, d, J=8.3 Hz). MS m/z 401.2 (M+H)$^+$.

Example 7

Benzamide, N-[1-(R)-(4-fluorophenyl)ethyl]-4-[[(2S,3S,4R,5S)-3,4,5-trihydroxy-2-(hydroxymethyl)-1-piperidinyl]methyl]-,

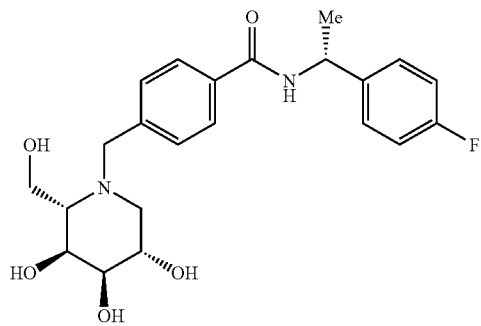

To a mixture of 3,4,5-piperidinetriol, 2-(hydroxymethyl)-, (2S,3S,4R,5S) (50 mg, 0.31 mmol) and (polystyrylmethyl) trimethylammonium cyanoborohydride (178 mg, 0.76 mmol) in 10% acetic acid in methanol (2 ml) was added N-[1-(R)(4-fluorophenyl)ethyl]-4-formylbenzamide (207 mg, 0.76 mmol) and the reaction mixture was stirred at room temperature overnight. The reaction mixture was purified using a plug of acidic Dowex 50WX-12 resin (3 g) (which had been pre-washed with 10% aqueous hydrochloric acid). The resin was eluted with methanol (25 ml) to remove all non-basic side products. The desired compound was then eluted using a solution of 2:2:1 methanol/water/ammonium hydroxide (100 ml). The resulting solution was concentrated to a small volume (1 ml) and freeze dried to afford the title compound as a white solid, 40 mg (31%). $^1$H NMR (d4-methanol) δ 1.55 (3H, d, J=7.1 Hz), 2.52 (1H, dd, J=6.8 and 12.0 Hz), 2.64 (1H, dd, J=3.8 and 12.0 Hz), 2.77 (1H, ddd, J=4.5, 5.1 and 5.9 Hz), 3.64 (1H, dd, J=3.4 and 6.4 Hz), 3.67 (1H, d, J=14 Hz), 3.74 (1H, ddd, J=3.8, 6.4 and 6.8 Hz), 3.83 (1H, dd, J=5.1 and 11.5 Hz), 3.91 (1H, dd, J=4.5 and 11.5 Hz), 3.96 (1H, dd, J=3.4 and 6.0 Hz), 4.12 (1H, d, J=14 Hz), 5.22 (1H, q, J=7.1 Hz), 7.05 (2H, dd, J=8.7 and 8.9 Hz), 7.41 (2H, dd, J=5.6 and 8.7 Hz), 7.50 (2H, d, J=8.1 Hz), 7.79 (2H, d, J=8.1 Hz). MS m/z 419.1 (M+H)$^+$.

Example 8

3,4,5-Piperidinetriol, 2-(hydroxymethyl)-1-[(2-phenyl-2H-1,4-benzoxazin-3(4H)-one-6-yl)methyl]-, (2S,3S,4R,5S)

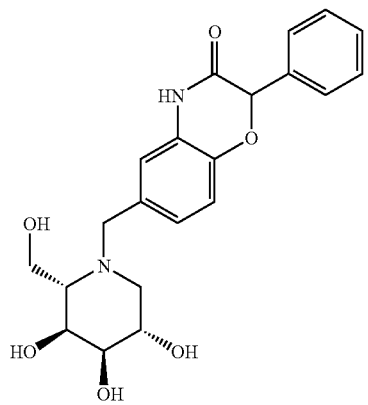

To a mixture of 3,4,5-piperidinetriol, 2-(hydroxymethyl)-, (2S,3S,4R,5S) (50 mg, 0.31 mmol), 2-phenyl-2H-1,4-benzoxazin-3(4H)-one-6-carbaldehyde (230 mg, 0.91 mmol) and (polystyrylmethyl)trimethylammonium cyanoborohydride (300 mg, 1.31 mmol) in methanol (2 ml) was added acetic acid (0.2 ml). The resultant mixture was stirred at room temperature for 16 h. The crude reaction mixture was purified using a plug of acidic Dowex 50×4-200 resin (1 g) (which had been pre-washed with methanol (10 ml)). The resin was eluted with methanol (25 ml) to remove all non-basic side products. The desired compound was then eluted using a solution of 7:1 methanol/ammonium hydroxide (25 ml). The resulting solution was concentrated to a small volume (1 ml) and freeze dried. The freeze dried solid was further purified using silica chromatography (gradient elution 10 to 30% methanol/dichloromethane and 1% ammonia) to afford the title compound as a white solid (34 mg, 27%). $^1$H NMR (d4-methanol) δ 2.62 (1H, m), 2.75 (1H, m), 2.87 (1H, m), 3.66-4.11 (7H, m), 5.69 (1H, s), 6.94-7.05 (3H, m), 7.32-7.45 (5H, m). MS m/z 401.2 (M+H)$^+$.

Example 9

3,4,5-Piperidinetriol, 2-(hydroxymethyl)-1-[[4-[(4-chlorophenyl)methoxy]phenyl]methyl]-, (2S,3S,4R,5S)

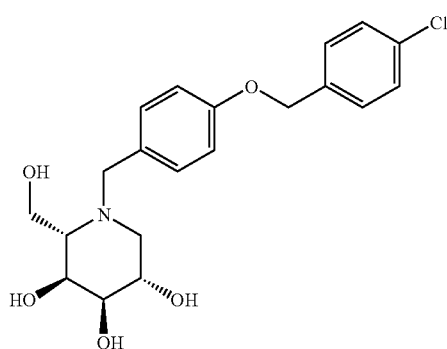

To a mixture of 3,4,5-piperidinetriol, 2-hydroxymethyl)-(2S,3S,4R,5S) (57 mg, 0.35 mmol) and (polystyrylmethyl) trimethylammonium cyanoborohydride (253 mg, 1.08 mmol) in 10% acetic acid in methanol (2 ml) was added 4-[(4-chlorophenyl)methoxy] benzaldehyde (280 mg, 1.13 mmol) and the reaction mixture was stirred at room temperature for two days. The reaction mixture was purified using a plug of acidic Dowex 50WX-12 resin (1 g), which had been pre-washed with methanol. The resin was r eluted with methanol (25 ml) and acetone (100 ml) to remove all non-basic side products. The desired compound was eluted using a solution of 7:1 methanol/ammonium hydroxide (50 ml). The resulting solution was concentrated, re-dissolved in methanol and pre-adsorbed onto silica gel. The product was then eluted through a silica gel column using methanol as solvent, concentrated to a gum, and freeze dried to afford the title compound as a white solid (64 mg, 46%). $^1$H NMR (d4-methanol) δ 2.51 (1H, m), 2.63 (1H, m), 2.74 (1H, m), 3.53-4.0 (7H, m), 5.05 (2H, s), 6.93 (2H, d, J=8.7 Hz), 7.29 (2H, d, J=8.7 Hz), 7.37 (2H, d, J=8.5 Hz), 7.43 (2H, d, J=8.5 Hz). MS m/z 394.1, 396.1 (M+H)$^+$.

Example 10

3,4,5-Piperidinetriol, 2-(hydroxymethyl)-1-[[4[(4-fluorophenyl)methoxy]phenyl]methyl]-, (2S,3S,4R,5S)

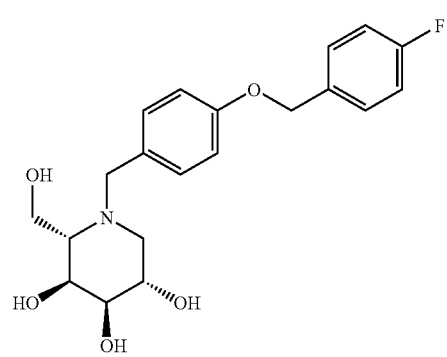

To a mixture of 3,4,5-piperidinetriol, 2-(hydroxymethyl)-(2S,3S,4R,5S) (57 mg, 0.35 mmol) and (polystyrylmethyl)trimethylammonium cyanoborohydride (250 mg, 1.07 mmol) in 10% acetic acid in methanol (2 ml) was added 4-[(4-fluorophenyl)methoxy]benzaldehyde (250 mg, 1.08 mmol) and the reaction mixture was stirred at room temperature for two days. The reaction mixture was purified using a plug of acidic Dowex 50WX-12 resin (1 g), which had been pre-washed with methanol. The resin was eluted with methanol (25 ml) and ethyl acetate (100 ml) to remove all non-basic side products. The desired compound was eluted using a solution of 7:1 methanol/ammonium hydroxide (100 ml). The resulting solution was concentrated, re-dissolved in methanol and pre-adsorbed onto silica gel. The product was then eluted through a silica gel column using methanol as solvent, concentrated to a gum, and freeze dried to afford the title compound as a white solid (56 mg, 42%). $^1$H NMR (d4-methanol) δ 2.57 (1H, m), 2.69 (1H, m), 2.80 (1H, m), 3.60-4.10 (7H, m), 5.05 (2H, s), 6.95 (2H, d, J=8.5 Hz), 7.09 (2H, m), 7.31 (2H, d, J=8.5 Hz), 7.45 (2H, m). MS m/z 378.1 (M+H)$^+$.

Biological Assays

The compounds of the invention may be tested for their biological activity in the following assays:

Inhibition of GCS

The assay for inhibition of GCS was performed essentially as described in Platt et al., J. Biol. Chem., (1994), 269, 27108, the enzyme source being human recombinant GCS expressed in insect cells.

Inhibition of non-lysosomal-β-glucocerebrosidase

The assay for inhibition of non-lysosomal-β-glucocerebrosidase was essentially carried out as described in Overkleeft, H. S. et al., J. Biol. Chem., (1998) 273, 26522-26527 with the following differences: whole cell extracts of MCF7 (a human breast carcinoma cell line) was used as the source of the enzyme instead of splenic membrane suspensions; 5mM instead of 3Mm, 4-MU β-glucoside was used as substrate and 0.2M citrate/phosphate (pH 5.8) was used instead of McIlvaine buffer.

Table I shows $IC_{50}$ data for compounds of the invention against human GCS and non-lysosomal-β-glucocerebrosidase enzymes.

TABLE I

| Compound | Inhibition of GCS ($IC_{50}$ μM) | Inhibition of non-lysosomal-β-glucocerebrosidase ($IC_{50}$ μM) |
|---|---|---|
| Example 1 | 2.20 | 100.00 |
| Example 2 | 0.66 | 9.40 |
| Example 3 | 7.20 | 14.90 |
| Example 4 | 0.62 | 1.93 |
| Example 7 | 4.70 | >100.00 |

Estimating the Cell-Based $Ic_{50}$ for GCS Inhibition by Measuring Glucosylceramide (GlcCer) Depletion Human mammary epithelial cells (MCF-7) were cultured for 5-7 days, with varying concentrations of a compound of the invention to be tested (0; 0.01; 0.05; 0.25; 1.25 and 6.25 μM). The cells were harvested and the total cellular lipids extracted. Neutral glycolipids were separated by partitioning in a DIPE/1-butanol/saline suspension, according to methods well known to those skilled in the art. The neutral glycolipid extracts were then separated by High-Performance Thin Layer Chromatography (HPTLC), using non-polar TLC conditions (chloroform:methanol: 0.2% $CaCl_2$: 65:35:8), according to methods well known to those skilled in the art GlcCer bands were visualized and the TLC plates were scanned immediately. Scion Image software was then used to quantify GlcCer in the samples relative to a GlcCer standard. This enabled a cell-based $IC_{50}$ to be calculated for compounds of the invention for GCS inhibition, as shown in the Table II.

Table II shows cell-based $IC_{50}$ data for compounds of the invention against human GCS.

TABLE II

| Compound | Inhibition of GCS Cellular-based ($IC_{50}$ μM) |
|---|---|
| Example 2 | <0.10 |
| Example 6 | 1.00 |

The invention claimed is:

1. A compound of formula (I) in free or pharmaceutically acceptable salt form:

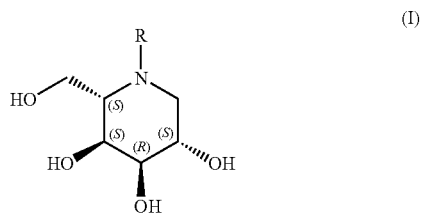

wherein

R is —$C_{1-3}$ alkylAr$^1$ where Ar$^1$ is phenyl;

wherein phenyl is substituted by one or more substituents selected from CN, CON(R$^1$)$_2$, SO$_n$R$^2$, SO$_2$N(R$^1$)$_2$, N(R$^5$)$_2$, N(R$^1$)COR$^2$, N(R$^1$)SO$_n$R$^2$, $C_{0-6}$ alkylAr$^2$, $C_{2-6}$ alkenylAr$^2$ and $C_{3-6}$ alkynylAr$^2$ wherein one or more of the —$CH_2$— groups of the alkyl chain may be replaced with a heteroatom selected from O, S and NR$^3$, provided that when the heteroatom is O, at least two —$CH_2$— groups separate it from any additional O atom in the alkyl chain; or two adjacent substituents on the Ar$^1$ phenyl may together form a fused 5- or 6-membered saturated or unsaturated ring wherein the ring optionally contains 1 or 2 heteroatoms selected from O, S and NR$^4$ and is optionally substituted by one or more substituents selected from, an oxo group, $C_{1-6}$ alkyl and $C_{0-3}$ alkylAr$^4$;

and the Ar$^1$ phenyl is optionally substituted by one or more additional substituents selected from F, Cl, Br, $CF_3$, $OCF_3$, OR$^3$ and $C_{1-6}$ alkyl;

R$^1$ is H, $C_{1-6}$ alkyl optionally substituted by OH, Ar$^3$, or $C_{1-6}$ alkylAr$^3$, or the group N(R$^1$)$_2$ may form a 5- to 10-membered heterocyclic group optionally containing one or more additional heteroatoms selected from O, S and NR$^3$ and is optionally substituted by an oxo group;

R$^2$ is $C_{1-6}$ alkyl optionally substituted by OH, Ar$^3$, or $C_{1-6}$ alkylAr$^3$;

R$^3$ is H, or $C_{1-6}$ alkyl;

R$^4$ is H, $C_{1-6}$ alkyl or $C_{0-3}$alkylAr$^4$;

R$^5$ is H, $C_{1-6}$ alkyl optionally substituted by OH, Ar$^3$, or $C_{1-6}$ alkylAr$^3$, or the group N(R$^5$)$_2$ may form a 5- to 10-membered heterocyclic group optionally containing one or more additional heteroatoms selected from O, S and NR$^3$ and is optionally substituted by an oxo group;

Ar$^2$ and Ar$^3$ are independently phenyl or a 5- to 10-membered heteroaryl group containing up to 3 heteroatoms selected from O, S and NR$^3$, which may be optionally substituted by one or more substituents selected from F, Cl, Br, CN, $CF_3$, $OCF_3$, $OR^3$ and $C_{1-6}$ alkyl;

$Ar^4$ is phenyl or pyridyl either of which may be optionally substituted by one or more substituents selected from F, Cl, Br, CN, $CF_3$, $OCF_3$, $OR^3$ and $C_{1-6}$ alkyl;

and n=0, 1 or 2.

2. The compound as defined in claim 1 wherein R is $C_1$alkyl$Ar^1$.

3. The compound as defined in claim 1, wherein $Ar^1$ is phenyl, wherein phenyl is substituted as defined in claim 1.

4. The compound as defined in claim 1, wherein $Ar^1$ is phenyl, wherein phenyl is substituted by one or more substituents selected from CN, $CON(R^1)_2$, $N(R^5)_2$, and $C_{0-6}$ alkyl$Ar^2$ wherein one or more of the —$CH_2$— groups of the alkyl chain may be replaced with a heteroatom selected from O, S and $NR^3$, provided that when the heteroatom is O, at least two —$CH_2$— groups separate it from any additional O atom in the alkyl chain, or two adjacent substituents on the $Ar^1$ phenyl may together form a fused 5- or 6-membered saturated or unsaturated ring wherein the ring optionally contains 1 or 2 heteroatoms selected from O and $NR^4$ and is optionally substituted by one or more substituents selected from, an oxo group, $C_{1-6}$ alkyl and $C_{0-3}$ alkyl$Ar^4$, and the $Ar^1$ phenyl is optionally substituted by one or more additional substituents selected from F, Cl, Br, $CF_3$, $OCF_3$, $OR^3$ and $C_{1-6}$ alkyl.

5. The compound as defined in claim 1, wherein $Ar^1$ is phenyl, wherein phenyl is substituted by one or more substituents selected from CN, $CON(R^1)_2$, $N(R^5)_2$, and $C_{0-6}$ alkyl$Ar^2$ wherein one or more of the —$CH_2$— groups of the alkyl chain may be replaced with O, provided that at least two —$CH_2$—groups separate it from any additional O atom introduced into the alkyl chain and the $Ar^1$ phenyl is optionally substituted by one or more additional substituents selected from F, Cl, Br, $CF_3$, $OCF_3$, $OR^3$ and $C_{1-6}$ alkyl.

6. The compound as defined in claim 1, wherein $Ar^2$ is phenyl which is optionally substituted by one or more substituents selected from F, Cl, Br, CN, $CF_3$, $OCF_3$, $OR^3$ and $C_{1-6}$ alkyl.

7. The compound as defined in claim 1, wherein $R^1$ is H or $C_{1-6}$ alkyl$Ar^3$.

8. The compound as defined in claim 1, wherein $R^4$ is H or $C_{1-6}$ alkyl.

9. The compound as defined in claim 1, wherein $Ar^3$ is phenyl which may be optionally substituted by one or more substituents selected from F, Cl, Br, CN, $CF_3$, $OCF_3$, $OR^3$ and $C_{1-6}$ alkyl.

10. The compound as defined in claim 1 wherein $R^5$ is $C_{1-6}$ alkyl.

11. The compound selected from

Benzamide, N-[(4-fluorophenyl)methyl]-4-[[2S,3S,4R,5S)-3,4,5-trihydroxy-2-(hydroxymethyl)-1-piperidinyl]methyl]-;

3,4,5-Piperidinetriol, 2-(hydroxymethyl)-1-[[4-(phenylmethoxy)phenyl]methyl]-,(2S,3S,4R,5S);

Benzamide, N-[1-(S)-(phenyl)ethyl]-4-[[(2S,3S,4R,5S)-3,4,5-trihydroxy-2-(hydroxymethyl)-1-piperidinyl]methyl]-;

3,4,5-Piperidinetriol, 1-[(3-cyano-4-(dipropylamino)phenyl)methyl]-2-(hydroxymethyl)-, (2S,3S,4R,5S);

Benzamide, N-[1-(S)-(4-fluorophenyl)ethyl]-4-[[2S,3S,4R,5S)-3,4,5-trihydroxy-2-(hydroxymethyl)-1-piperidinyl]methyl]-;

Benzamide, N-[1-(R)-(phenyl)ethyl]-4-[[2S,3S,4R,5S)-3,4,5-trihydroxy-2-(hydroxymethyl)-1-piperidinyl]methyl]-;

Benzamide, N-[1-(R)-(4-fluorophenyl)ethyl]-4-[[2S,3S,4R,5S)-3,4,5-trihydroxy-2-(hydroxymethyl)-1-piperidinyl]methyl]-;

3,4,5-Piperidinetriol, 2-(hydroxymethyl)-1-[(2-phenyl-2H-1,4-benzoxazin-3(4H)-one-6-yl)methyl]-, (2S,3S,4R,5S);

3,4,5-Piperidinetriol, 2-(hydroxymethyl)-1-[[4-[(4-chlorophenyl)methoxy]phenyl]methyl]-, (2S,3S,4R,5S);

3,4,5-Piperidinetriol, 2-(hydroxymethyl)-1-[[4-[(4-fluorophenyl)methoxy]phenyl]methyl]-, (2S,3S,4R,5S), in free or pharmaceutically acceptable salt form.

12. The pharmaceutical composition comprising a compound of formula (I) as defined in claim 1, together with one or more pharmaceutically acceptable carriers, excipients and/or diluents.

13. The process for the preparation of a compound of formula (I) as defined in claim 1, the process comprising:

a) reductive amination of an aldehyde of formula $R^5$CHO wherein $R^5$ is $C_{0-2}$ alkyl$Ar^1$ where $Ar^1$ is as defined in claim 1, with a compound of formula (II):

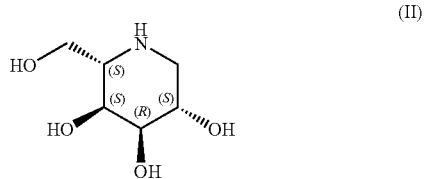

or b) deprotection of a compound of formula (III):

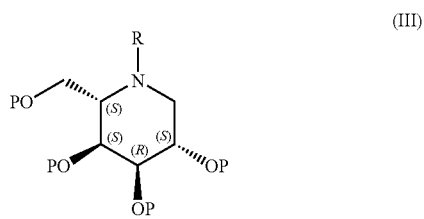

wherein R is as defined in claim 1 and P, which may be the same or different, are hydroxy protecting groups.

* * * * *